(12) United States Patent
Sieffert et al.

(10) Patent No.: US 9,202,164 B2
(45) Date of Patent: Dec. 1, 2015

(54) DOSE COUNTER AND MEDICATION DELIVERY DEVICE

(71) Applicants:Marcus A. Sieffert, London (GB); Scott Galea, London (GB)

(72) Inventors: Marcus A. Sieffert, London (GB); Scott Galea, London (GB)

(73) Assignee: Trudell Medical International, London (CA)

( * ) Notice: Subject to any disclaimer, the term of this patent is extended or adjusted under 35 U.S.C. 154(b) by 678 days.

(21) Appl. No.: 13/626,424

(22) Filed: Sep. 25, 2012

(65) Prior Publication Data

US 2013/0074833 A1    Mar. 28, 2013

Related U.S. Application Data

(60) Provisional application No. 61/539,188, filed on Sep. 26, 2011.

(51) Int. Cl.
*A61M 11/00* (2006.01)
*G06M 1/04* (2006.01)
(Continued)

(52) U.S. Cl.
CPC .............. *G06M 1/041* (2013.01); *A61M 15/009* (2013.01); *A61M 15/0073* (2014.02); *A61M 15/0076* (2014.02); *A61M 15/0081* (2014.02); *G06M 1/16* (2013.01); *G06M 1/22* (2013.01); *G06M 1/24* (2013.01); *Y10T 29/49863* (2015.01)

(58) Field of Classification Search
CPC .......... A61M 15/009; A61M 15/0068; A61M 15/007; A61M 15/0073; A61M 15/0076; A61M 15/0081; G06M 1/041; G06M 1/048
See application file for complete search history.

(56) References Cited

U.S. PATENT DOCUMENTS

| 5,020,527 A | 6/1991 | Dessertine |
| 5,505,195 A | 4/1996 | Wolf et al. |

(Continued)

FOREIGN PATENT DOCUMENTS

| EP | 1172122 A1 | 1/2002 |
| GB | 2398250 A | 8/2004 |

(Continued)

OTHER PUBLICATIONS

International Search Report and Written Opinion of the International Searching Authority for International Application No. PCT/IB2012/001869, dated Jan. 16, 2013, 15 pages.

*Primary Examiner* — Justine Yu
*Assistant Examiner* — Michael Tsai
(74) *Attorney, Agent, or Firm* — Brinks Gilson & Lione

(57) ABSTRACT

A dose counter includes a housing having an indicator member rotatably mounted in the housing. A drive gear is associated with the indicator member. The drive gear and a flexible support member include interfacing indexing features, with at least a portion of the support member being moveable toward and away from the drive gear. In another aspect, a movement limiter is operably engaged with the indicator member to prevent any rotation of the indicator member in response to actuations occurring between a predetermined number of actuations greater than one. In another aspect, a drive member includes a pawl portion and a biasing portion. The biasing portion is engageable with indicator member and biases the pawl outwardly relative to the indicator member along the axial direction as the drive member is moved from a preassembled position to an assembled position. Medicament devices including containers of medicament, together with methods of use and assembly, are also provided.

30 Claims, 8 Drawing Sheets

(51) Int. Cl.
    *A61M 15/00*     (2006.01)
    *G06M 1/16*     (2006.01)
    *G06M 1/22*     (2006.01)
    *G06M 1/24*     (2006.01)

(56) References Cited

U.S. PATENT DOCUMENTS

| | | | |
|---|---|---|---|
| 5,544,647 A | 8/1996 | Jewett et al. | |
| 5,582,162 A | 12/1996 | Petersson | |
| 5,687,710 A | 11/1997 | Ambrosio et al. | |
| 5,740,792 A | 4/1998 | Ashley et al. | |
| 5,826,571 A | 10/1998 | Casper et al. | |
| 5,829,434 A | 11/1998 | Ambrosio et al. | |
| 5,840,279 A | 11/1998 | Narodylo et al. | |
| 6,071,498 A | 6/2000 | Narodylo et al. | |
| 6,182,655 B1 | 2/2001 | Keller et al. | |
| 6,240,918 B1 | 6/2001 | Ambrosio et al. | |
| 6,283,365 B1 | 9/2001 | Bason | |
| 6,328,037 B1 | 12/2001 | Scarrott et al. | |
| 6,336,453 B1 | 1/2002 | Scarrott et al. | |
| 6,446,627 B1 | 9/2002 | Bowman et al. | |
| 6,655,381 B2 | 12/2003 | Keane et al. | |
| 6,679,251 B1 | 1/2004 | Gallem et al. | |
| 6,701,917 B2 | 3/2004 | O'Leary | |
| 6,718,972 B2 | 4/2004 | O'Leary | |
| 6,769,601 B2 | 8/2004 | Haikarainen et al. | |
| 6,926,002 B2 | 8/2005 | Scarrott et al. | |
| 6,953,039 B2 | 10/2005 | Scarrott et al. | |
| 6,978,780 B1 | 12/2005 | Marnfeldt et al. | |
| 7,047,964 B2 | 5/2006 | Bacon | |
| 7,107,988 B2 | 9/2006 | Pinon et al. | |
| 7,195,134 B2 | 3/2007 | Ouyang et al. | |
| 7,219,664 B2 | 5/2007 | Ruckdeschel et al. | |
| 7,331,340 B2 | 2/2008 | Barney | |
| 7,341,057 B2 | 3/2008 | Scarrott et al. | |
| 7,395,821 B2 | 7/2008 | Lulla et al. | |
| 7,448,342 B2 | 11/2008 | Von Schuckmann | |
| 7,516,738 B2 | 4/2009 | Scarrott et al. | |
| 7,540,282 B2 | 6/2009 | O'Leary | |
| 7,584,712 B2 | 9/2009 | Lu | |
| 7,600,512 B2 | 10/2009 | Lee et al. | |
| 7,621,273 B2 | 11/2009 | Morton et al. | |
| 7,650,883 B2 | 1/2010 | Scarrott et al. | |
| 7,757,688 B2 | 7/2010 | Scarrott et al. | |
| 7,827,989 B2 | 11/2010 | Butterworth et al. | |
| 7,854,226 B2 | 12/2010 | Pinon et al. | |
| 8,051,851 B2 | 11/2011 | Herder et al. | |
| 8,074,643 B2 | 12/2011 | Scarrott et al. | |
| 2002/0078950 A1 | 6/2002 | O'Leary | |
| 2002/0153005 A1 | 10/2002 | Scarrott et al. | |
| 2003/0178020 A1 | 9/2003 | Scarrott | |
| 2004/0089298 A1 | 5/2004 | Haikarainen et al. | |
| 2004/0255936 A1 | 12/2004 | Urbanus | |
| 2005/0011515 A1 | 1/2005 | Lee et al. | |
| 2005/0087191 A1 | 4/2005 | Morton et al. | |
| 2005/0126469 A1 | 6/2005 | Lu | |
| 2005/0183723 A1 | 8/2005 | Pinon et al. | |
| 2006/0037612 A1 | 2/2006 | Herder et al. | |
| 2006/0150971 A1 | 7/2006 | Lee et al. | |
| 2006/0185672 A1 | 8/2006 | Pinon et al. | |
| 2006/0231093 A1 | 10/2006 | Burge et al. | |
| 2007/0181120 A1 | 8/2007 | Wright et al. | |
| 2007/0295329 A1 | 12/2007 | Lieberman et al. | |
| 2008/0060643 A1 | 3/2008 | Hodson et al. | |
| 2008/0066742 A1 | 3/2008 | Hodson et al. | |
| 2008/0066750 A1 | 3/2008 | Minshull et al. | |
| 2008/0127971 A1 | 6/2008 | King et al. | |
| 2009/0173346 A1* | 7/2009 | Stuart et al. | 128/203.12 |
| 2009/0272312 A1* | 11/2009 | Nuttall | 116/201 |
| 2010/0016908 A1 | 1/2010 | Martin et al. | |
| 2010/0065649 A1 | 3/2010 | Bowman et al. | |
| 2010/0083964 A1 | 4/2010 | Brown et al. | |
| 2010/0163031 A1* | 7/2010 | Morton et al. | 128/203.12 |
| 2010/0192946 A1 | 8/2010 | Oi et al. | |
| 2010/0263665 A1 | 10/2010 | Brown et al. | |
| 2010/0313884 A1 | 12/2010 | Elliman | |
| 2012/0255548 A1 | 10/2012 | Denny et al. | |

FOREIGN PATENT DOCUMENTS

| | | |
|---|---|---|
| WO | WO 92/17231 A1 | 10/1992 |
| WO | WO 95/26769 A1 | 10/1995 |
| WO | WO 97/30743 A2 | 8/1997 |
| WO | WO 98/48874 A1 | 11/1998 |
| WO | WO 99/57019 A2 | 11/1999 |
| WO | WO 01/31578 A1 | 5/2001 |
| WO | WO 01/37909 A1 | 5/2001 |
| WO | WO 2006/062448 A1 | 6/2006 |
| WO | WO 2007/012861 A1 | 2/2007 |
| WO | WO 2007/031740 A1 | 3/2007 |
| WO | WO 2007/077450 A2 | 7/2007 |

* cited by examiner

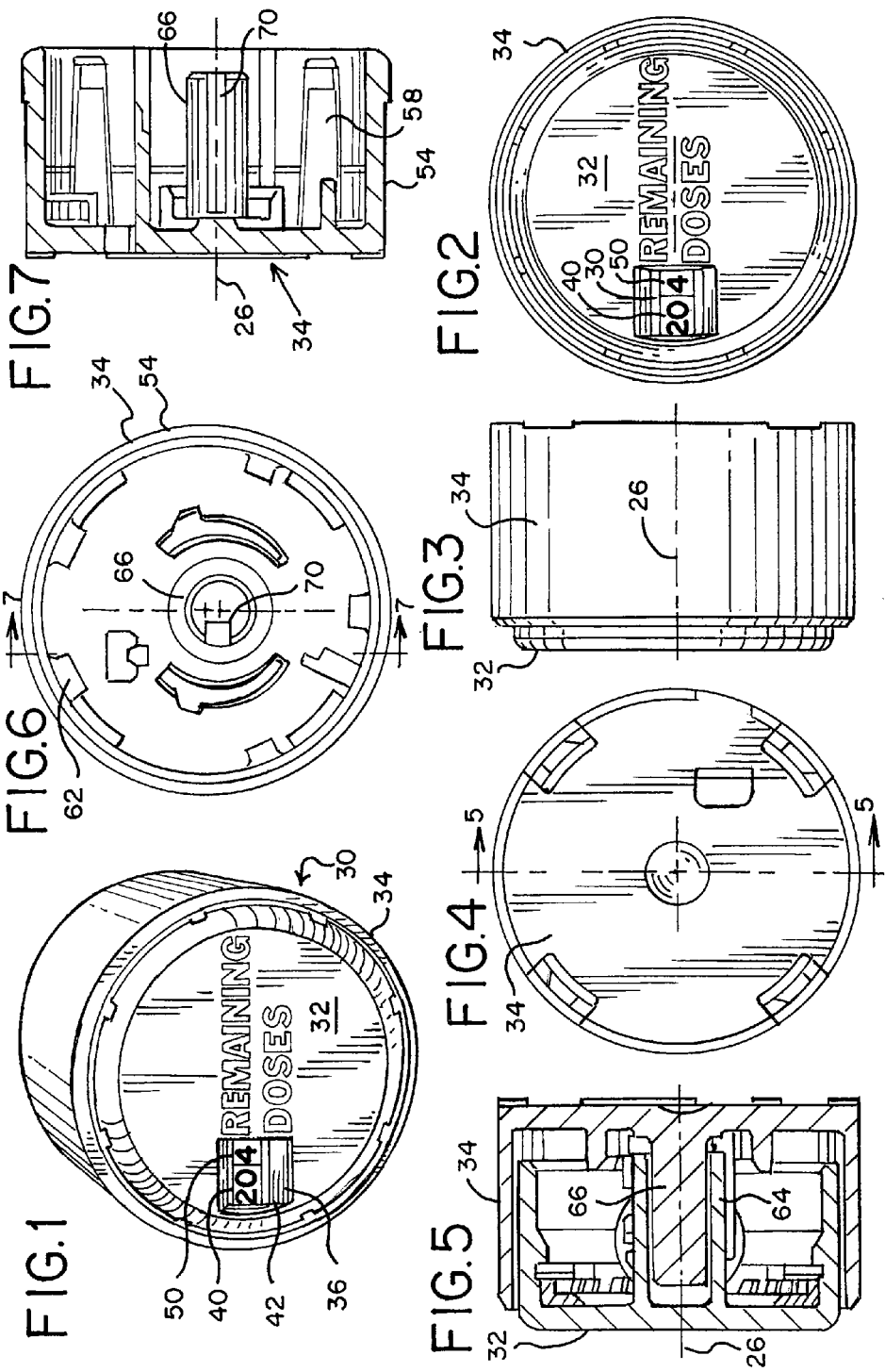

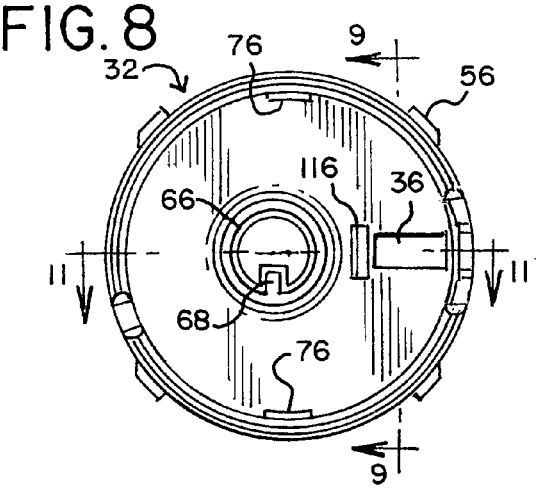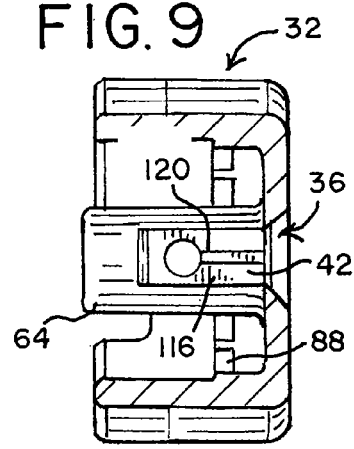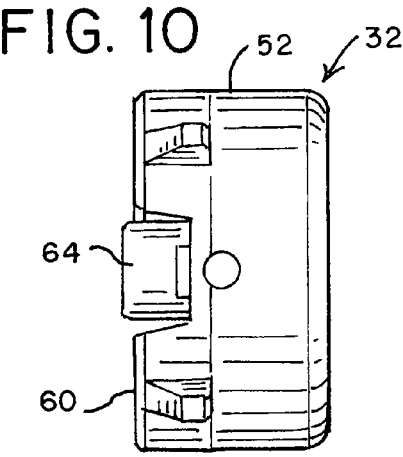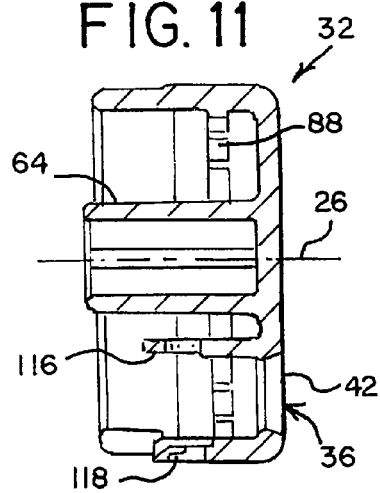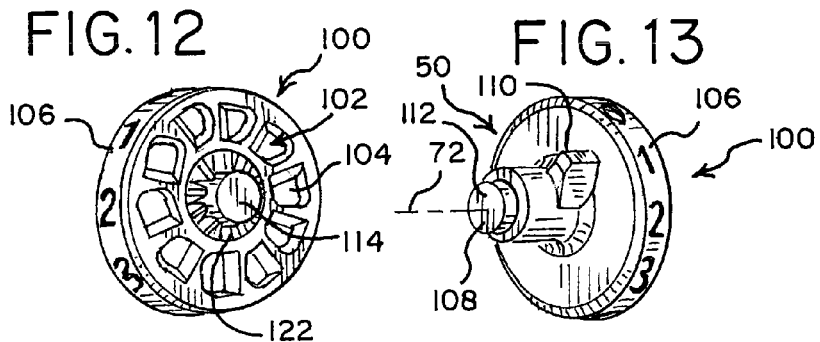

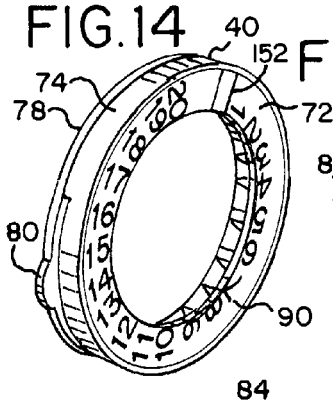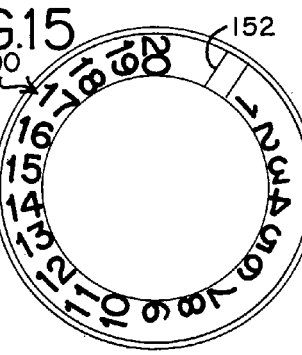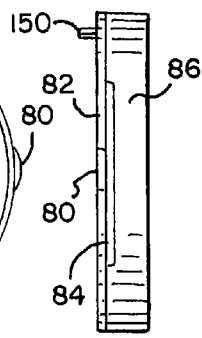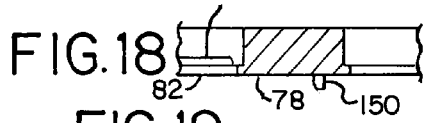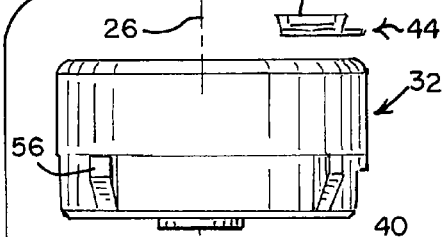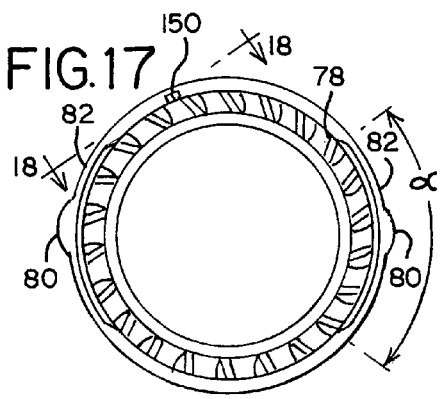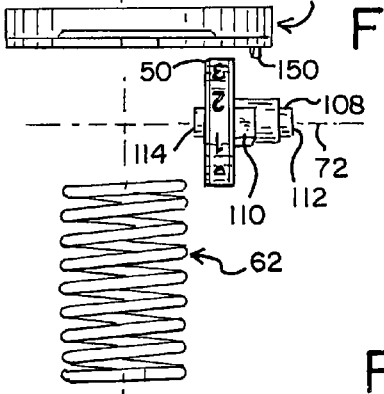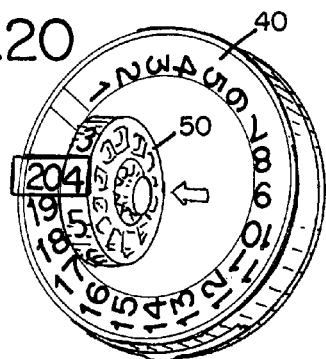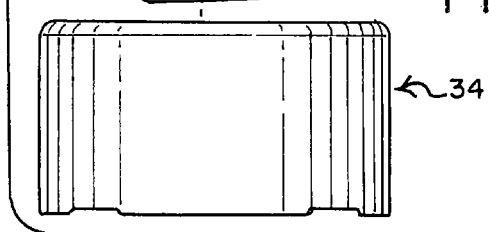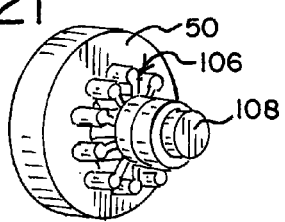

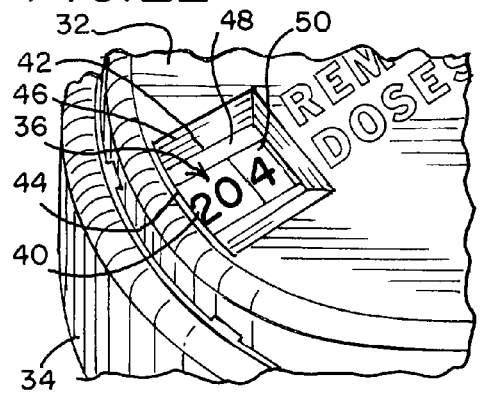
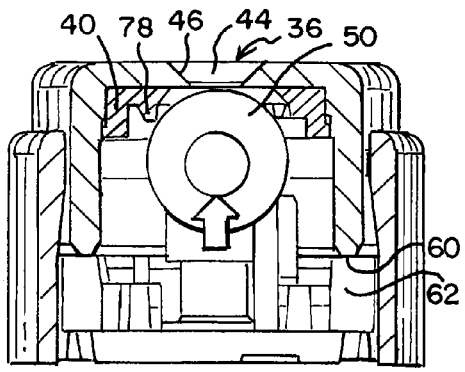
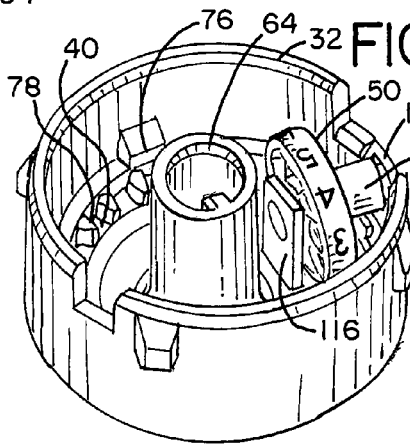
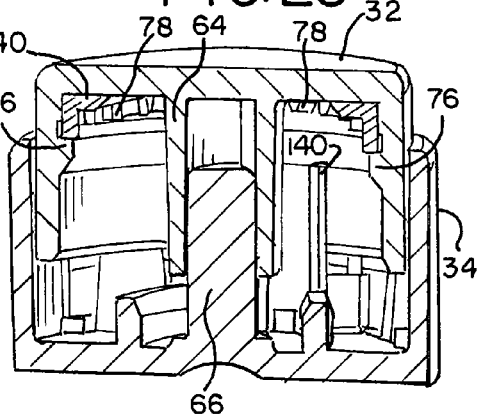
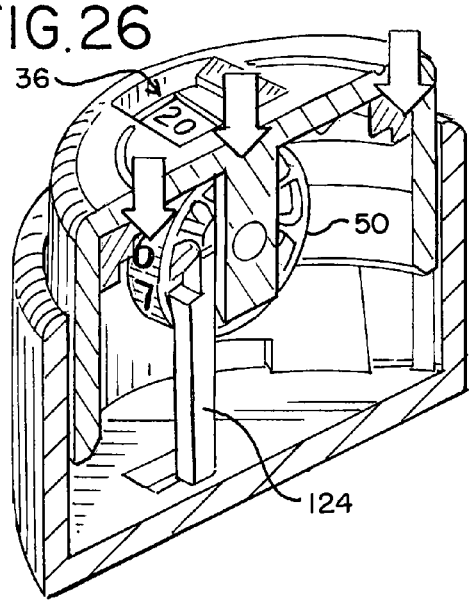
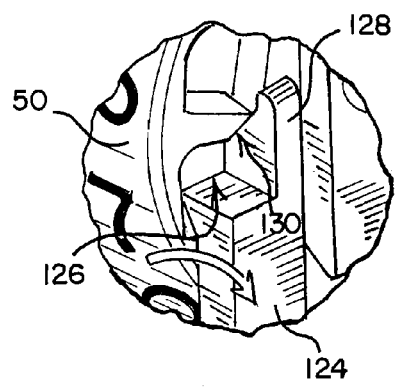

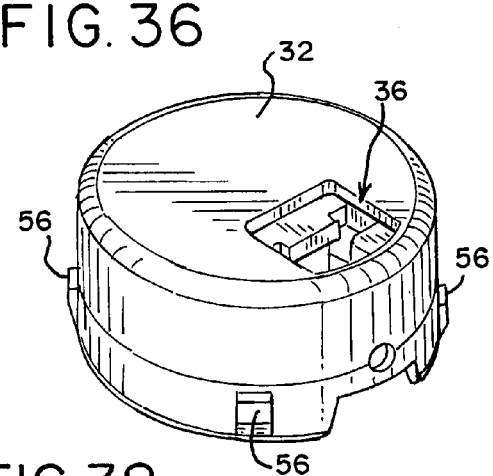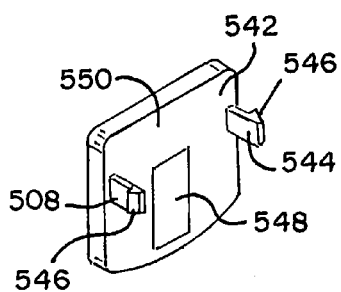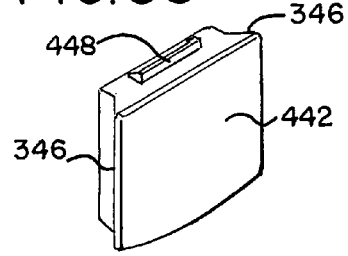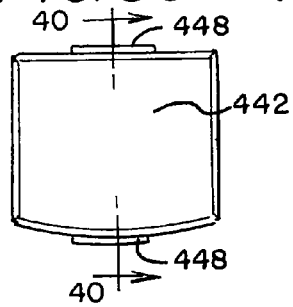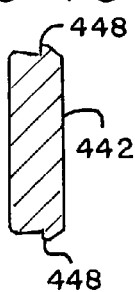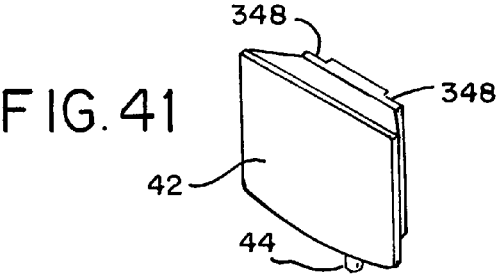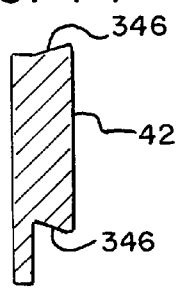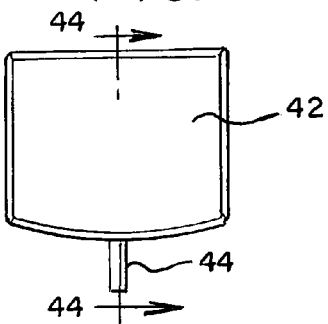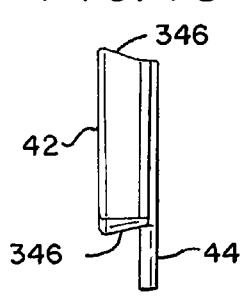

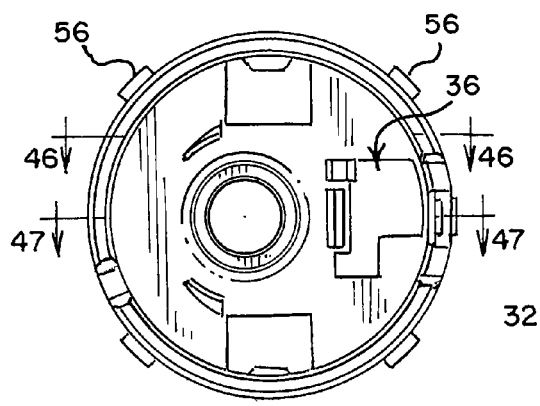
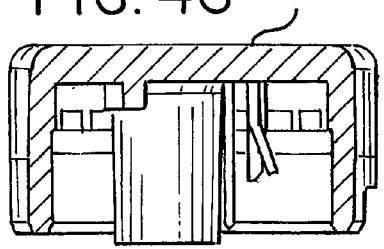
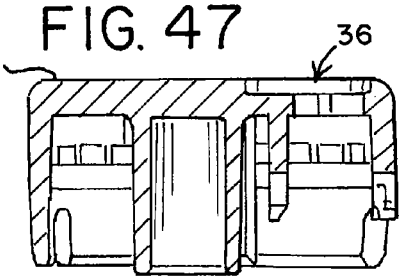
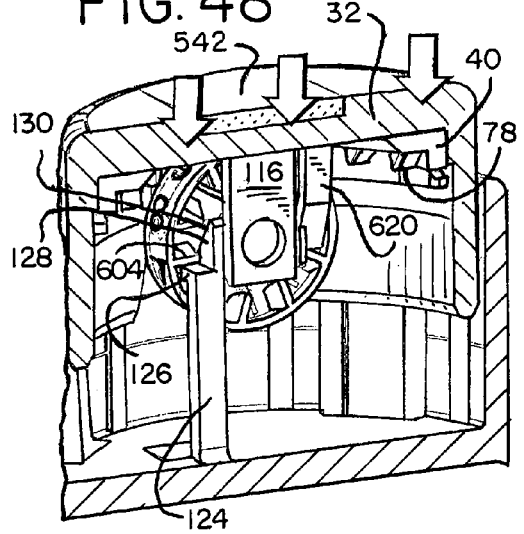
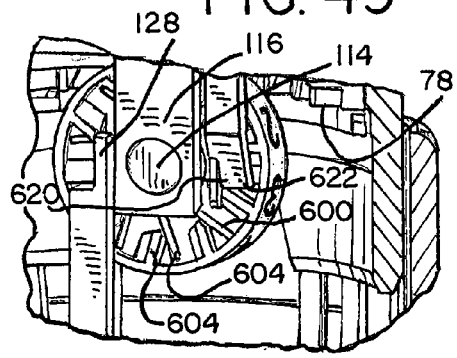
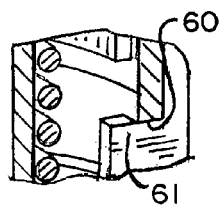
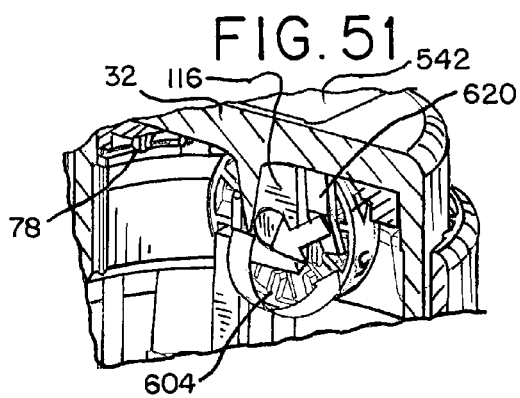

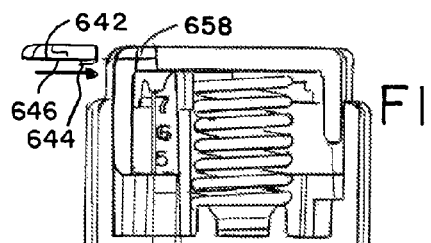
FIG. 52
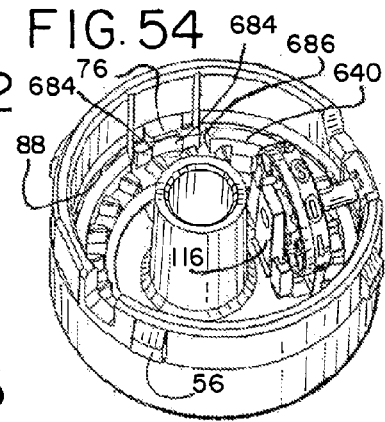
FIG. 54
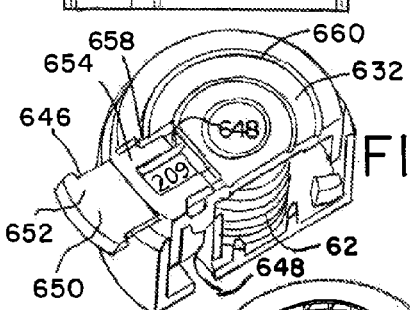
FIG. 53
FIG. 55  FIG. 56
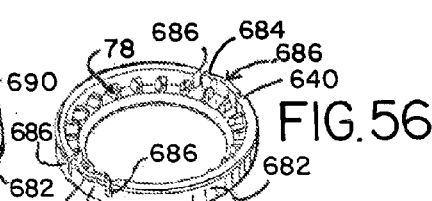
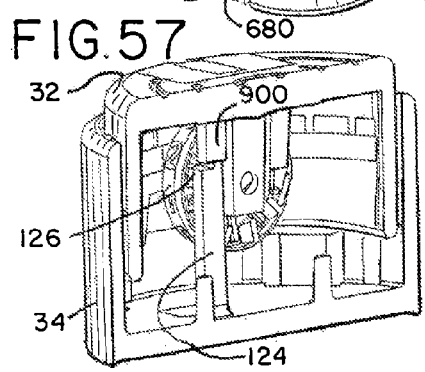
FIG. 57  FIG. 58
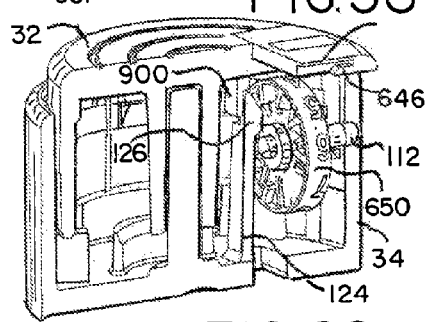
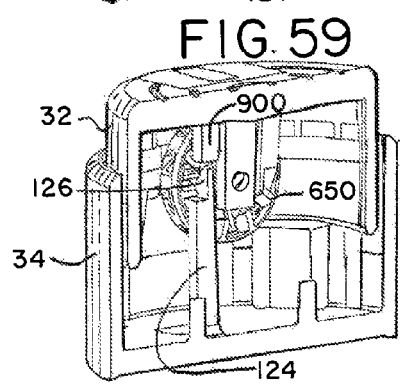
FIG. 59  FIG. 60
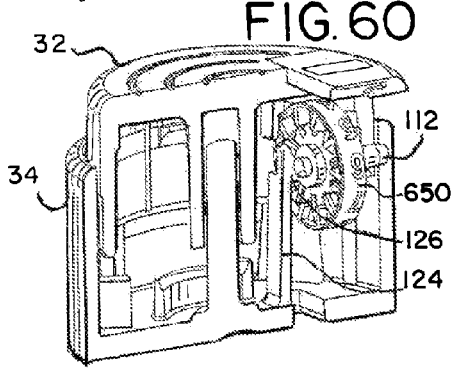

DOSE COUNTER AND MEDICATION DELIVERY DEVICE

This application claims the benefit of U.S. Provisional Application Ser. No. 61/539,188, filed Sep. 26, 2011 and entitled DOSE COUNTER AND MEDICATION DELIVERY DEVICE, the entire disclosure of which is hereby incorporated herein by reference.

TECHNICAL FIELD

The present invention relates generally to a dose counter, and in particular, to a dose counter for use with a medication delivery device, including without limitation a pressurized metered dose inhaler.

BACKGROUND

Medicament dispensing devices have been developed that include a dose indicating device to indicate the number of metered doses that have been dispensed from the device, or to indicate the number of doses remaining therein. For example, patients may have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

Typically, a conventional aerosol container includes a body and a valve stem which can be depressed relative to the body so as to emit the metered dose of aerosol and medicament. The container typically is supplied with a predetermined number of metered doses, generally on the order of about 200, such that the counting of the number of valve stem depressions, and corresponding number of dispensed metered doses, can be directly correlated with the number of doses remaining in the container.

In operation, the container is typically received within a housing of the inhalation device, wherein the valve is brought into engagement with a support block in the housing. The user administers the medicament by moving the container relative to the housing so as to depress the valve stem and internal valve and-thereby release a metered dose, which is typically administered to the user through a port or mouthpiece extending from the housing. After the dose is administered, the valve stem, which is typically spring loaded, biases the container away from the support block so as to again move the container relative to the housing. In this way, a metered dose of medicament is administered by each cycle of linear reciprocal movement of the container relative to the housing.

Some actuator boots, or other devices attached to the medicament container, have indicating devices that convert the linear reciprocal movement of the container relative to the housing into a one-way, or single-cycle, movement of an indicator, wherein the indicator identifies the relative fullness of the container, the number of metered doses remaining therein or the number of doses already administered. Although these actuator boots with indicators, or separate indicator devices, have provided the advantage of generally being able to keep track of the number of dosages, there remains room for improvement.

For example, indicating devices of this nature may include complex moving parts which can be difficult to assemble and expensive to manufacture. In addition, such devices may be susceptible to counting inaccuracies due to the configuration of the indexing or mating parts, for example in response to the device being dropped or falling to the ground. In addition, such devices may take excessive amounts of space, or require relative large housings, which may interfere with the proper actuation of the device, or make the device more susceptible to counting accuracies.

SUMMARY

Briefly stated, a dose counter includes a housing having an indicator member rotatably mounted in the housing. The indicator member is configured with dosage indicia. A drive gear is associated with the indicator member and is rotatable about an axis defining an axial direction. The drive gear includes a plurality of first indexing features disposed radially about the axis. A support member rotatably supports the drive gear. The support member includes at least one second indexing feature releasably engaging at least one of the first indexing features. At least a portion of the support member is moveable toward and away from the drive gear along the axial direction as the drive gear is rotated relative to the support member. The at least one second indexing feature is successively engaged with the first indexing features as the drive gear is rotated relative to the support member. In another embodiment, a container of medicament may be coupled to the dose counter.

In another aspect, a dose counter includes a housing and an indicator member rotatably mounted in the housing. The indicator member is configured with dosage indicia. The indicator member is rotatable upon a predetermined number of actuations, wherein the predetermined number is greater than one. A movement limiter is operably engaged with the indicator member to prevent any rotation of the indicator member in response to actuations occurring between the predetermined number of actuations. In another embodiment, a container of medicament may be coupled to the dose counter.

In another embodiment, the movement limiter is reciprocally moveable along the axial direction relative to the indicator member in response to each of the actuations occurring between the predetermined number of actuations.

In another aspect, a dose counter includes an indicator member rotatable about an axis of rotation extending in an axial direction. The indicator member includes a face defining a circumferential perimeter and a plurality of teeth radially arranged on the face relative to the axis. A drive member includes a pawl portion shaped to engage at least one of the plurality of teeth, and a biasing portion. The drive member is moveable relative to the indicator member from a preassembled position, wherein the pawl portion is positioned outside of the perimeter, to an assembled position, wherein the pawl is positioned inside of the perimeter. The biasing portion is engageable with indicator member and biases the pawl outwardly relative to the indicator member along the axial direction as the drive member is moved from the preassembled position to the assembled position.

In yet another aspect, a method of assembling a dose counter includes moving a drive member relative to an indicator member along a first direction, engaging a biasing portion of the drive member with the indicator member and biasing the drive member in a second direction substantially perpendicular to the first direction, releasing the drive member, and engaging the indicator member with a pawl portion of the drive member.

The various aspects and embodiments provide advantages over other dose counters and medicament delivery devices. For example and without limitation, the resilient support member and drive gear, with their interfacing indexing features, eliminates the need for an additional non-return member, which may occupy additional space in the housing. In addition, the support member may bias the drive gear, and an indicator member associated therewith, against a second indicator member, thereby maintaining a close relationship therebetween as they are viewed by the user.

The movement limiter also presents various advantages. For example and without limitation, the movement limiter acts as a fall arrestor, which prevents the indicator member from inadvertently advancing when subjected to a large external force, for example due to a fall. Such forces may overcome conventional indexing devices, which rely on friction or interference fits.

The drive member, with its pawl and biasing portions, also provides various advantages. For example and without limitation, the biasing portion allows the pawl to be positioned inside the perimeter of the indicator member, thereby reducing the overall space required the device thereby allowing the device to be made more compact. At the same time, the biasing portion eliminates the need for expensive and complicated tooling required to effectuate the installation of the pawl inside the perimeter, but rather relies simply on the installation forces created during the assembly of the housing to properly position the pawl.

The present invention, together with further objects and advantages, will be best understood by reference to the following detailed description taken in conjunction with the accompanying drawings.

BRIEF DESCRIPTION OF THE DRAWINGS

FIG. 1 is a top perspective view of a dose counter.
FIG. 2 is a top view of the dose counter shown in FIG. 1.
FIG. 3 is a side view of the dose counter shown in FIG. 1.
FIG. 4 is a bottom view of the dose counter shown in FIG. 1.
FIG. 5 is a cross-sectional view of the dose counter shown in FIG. 4 taken along line 5-5.
FIG. 6 is a top view of a base housing component.
FIG. 7 is a cross-sectional view of the base housing component shown in FIG. 6 taken along line 7-7.
FIG. 8 is a bottom view of a cap housing component.
FIG. 9 is a cross-sectional view of the cap housing component shown in FIG. 8 taken along line 9-9.
FIG. 10 is a side view of the cap housing component shown in FIG. 8.
FIG. 11 is a cross-sectional view of the cap housing component shown in FIG. 8 taken along line 11-11.
FIG. 12 is a first side perspective view of an indicator member having an integrated drive gear and indexing features.
FIG. 13 is an opposite side perspective view of the indicator member shown in FIG. 12 having a drive tooth.
FIG. 14 is a perspective view of an indicator member.
FIG. 15 is a top view of the indicator member shown in FIG. 14.
FIG. 16 is a side view of the indicator member shown in FIG. 14.
FIG. 17 is a bottom view of the indicator member shown in FIG. 14.
FIG. 18 is a partial cross-sectional side view of the indicator member shown in FIG. 17 taken along line 18-18.
FIG. 19 is an exploded side view of one embodiment of the dose counter.
FIG. 20 is a perspective view of the first and second indicator members.
FIG. 21 is a perspective view of an alternative embodiment of the first indicator member.
FIG. 22 is an enlarged, partial top perspective view of a dose counter viewing window.
FIG. 23 is a cross-sectional view showing the viewing window positioned relative to first and second indicator members.
FIG. 24 is a perspective view of a cap housing component with first and second indicator members coupled thereto.
FIG. 25 is a cross-sectional view of a dose counter configured with a movement limiter.
FIG. 26 is a cross-sectional perspective view of a dose counter with drive member configured with biasing and pawl portions.
FIG. 27 is an enlarged view of the biasing and pawl portions shown in FIG. 26.
FIG. 36 is a top, perspective view of a cap member.
FIG. 37 is a bottom perspective view of one embodiment of a viewing window pane member.
FIG. 38 is a top perspective view of an alternative embodiment of a viewing window pane member.
FIG. 39 is a top view of the viewing window pane member shown in FIG. 38.
FIG. 40 is a cross-sectional view of the viewing window pane member taken along line 40-40 of FIG. 39.
FIG. 41 is a top perspective view of an alternative embodiment of a viewing window pane member.
FIG. 42 is a top view of the viewing window pane member shown in FIG. 41.
FIG. 43 is a side view of the viewing window pane member shown in FIG. 41.
FIG. 44 is a cross-sectional view of the viewing window pane member taken along line 44-44 of FIG. 42.
FIG. 45 is a bottom view of one embodiment of a cap member.
FIG. 46 is a cross-sectional view of the cap member shown in FIG. 45 taken along line 46-46.
FIG. 47 is a cross-sectional view of the cap member shown in FIG. 45 taken along line 47-47.
FIG. 48 is a partial, interior perspective view of one embodiment of a dose counter.
FIG. 49 is a partial, interior perspective view of one embodiment of a dose counter during an actuation of the container and dose counter.

FIG. 50 is a partial, interior perspective view showing a cap member engaging a stop pad.

FIG. 51 is a partial, interior perspective view during a return phase of the dose counting actuation.

FIG. 52 is a cross-sectional, side view showing a window pane being applied to a dose counter.

FIG. 53 is a perspective view of the window pane being applied to the dose counter.

FIG. 54 is a bottom view of a cap member with indicator members coupled thereto.

FIG. 55 is a top perspective view of one embodiment of an indicator member.

FIG. 56 is a bottom perspective view of the indicator member shown in FIG. 55.

FIG. 57 is a partial, cut away of a dose counter in a drop condition

FIG. 58 is another partial, cut away of a dose counter in a drop condition.

FIG. 59 is a partial, cut away of a dose counter at the start of an actuation.

FIG. 60 is another partial, cut away of a dose counter at the start of an actuation.

DETAILED DESCRIPTION OF THE PRESENTLY PREFERRED EMBODIMENTS

Figure 31:
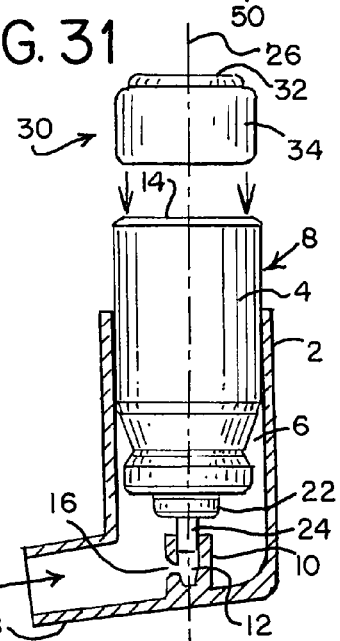
FIG. 31 is a partial cross-sectional view showing a dose counter being applied to a container of medicament coupled to an actuator.
Figure 32:
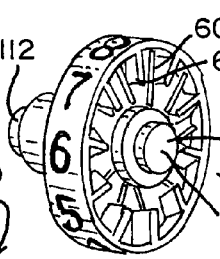
FIG. 32 is a perspective view of an alternative embodiment of an indicator member.

Referring to the drawings, and in particular FIG. 31, an aerosol dispenser 8 is shown as including a housing 2, or actuator boot, and a container 4 disposed therein. The housing has a longitudinally extending cavity 6 shaped to receive the container. A top portion of the housing is generally open such that the container can be inserted in the housing through opening and be installed therein with a bottom end 14 of the container protruding from the housing so as to be exposed to the user for actuation.

The terms "longitudinal" and "axial" as used herein relates to a length or lengthwise direction, including for example the direction of the reciprocal movement of the container relative to the housing, and of an indicating device cap member relative to a base member. The term "lateral" and variations thereof refer to a sideways direction. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa. Moreover, it should be understood that a user can use the container and dispenser in any number of positions, including but not limited to the preferred upright position shown in FIG. 31.

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. The term "transverse" means extending across an axis, and/or substantially perpendicular to an axis. It should be understood that the use of numerical terms "first," "second," "third," etc., as used herein does not refer to any particular sequence or order of components; for example "first" and "second" indicator members may refer to any sequence of such members, and is not limited to the first and second indicator members of a particular configuration unless otherwise specified.

As shown in FIG. 31, a cylindrical support block 10 having a well 12 is formed in a bottom portion of the housing. An orifice 16 penetrates the support block to communicate with a bottom portion of the well. In one embodiment, a mouthpiece 18, intended for insertion into the mouth of a patient, forms an exhaust port 20 that communicates with the orifice and well. The mouthpiece extends laterally from the housing 2 so as to facilitate insertion of the mouthpiece into the mouth of the patient.

The container 4 is cylindrical and has a hub 22 disposed on a top thereof. A valve stem 24 extends longitudinally from the hub. The valve stem 24 extends coaxially from the container 4 and is biased outwardly therefrom by a spring (not shown) mounted within the container. The container 4 is mounted in the housing 2 by press fitting the valve stem 24 in the well 12 of the support block 10.

In one embodiment, the container 4 is filled with a pressurized aerosol and medicament which is dispensed therefrom in specific metered doses by depressing or moving the valve stem 24 from an extended closed position to a depressed open position. A single metered dose is dispensed from the container 4 by each reciprocal, longitudinal movement of the valve stem 24 relative to main body of the container 4.

In operation, the opening of the valve stem 24 is effected by moving the container 4 reciprocally within the housing 2 along a longitudinal axis 26, defined by the valve stem 24 and the reciprocal movement of the container, by depressing the bottom end 14 of the container relative to the housing 2 so as to move the valve stem 24 to the open position as it is supported within the well 12 by the support block. As the valve stem 24 is moved to the open position, the container 4 dispenses a metered dose of aerosol and medicament through the well 12 and orifice 16. The aerosol and medicament are then transmitted to the patient through the exhaust port 20 of the mouthpiece 18 by way of either a self-generated or assisted airflow.

In other delivery systems, the housing and holder for the container are attached to a component having a chamber with an output end. Examples of these kinds of delivery systems are shown for example in U.S. Pat. No. 7,201,165, issued Apr. 10, 2007, U.S. Pat. No. 6,435,177, issued Aug. 20, 2002, U.S. Pat. No. 6,345,617, issued Feb. 12, 2002, U.S. Pat. No. 5,012,803, issued May 7, 1991, and U.S. Pat. No. 4,460,412, issued Sep. 11, 1984, all of which are hereby incorporated herein by reference. (No license, expressed or implied, is intended to be granted to either of these patents by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In one embodiment, the container 4 is intended to dispense a predetermined number of metered doses of medicament. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament.

Now generally referring to the Figures, a dose counter 30, otherwise referred to as a dose indicating device is shown. The indicating device indicates the number of metered doses that have been dispensed from or remain in the container. As shown in the embodiments of FIGS. 1-11, respectively, the indicating device includes an indicating device housing configured in one embodiment as a cap member 32 disposed in a base member 34. The base member is configured such that it can be mounted to the bottom 14 of the container. In one embodiment, shown in FIG. 31, the base member includes a convex, or curved bottom portion, or floor, which is shaped to be received in and to mate with the bottom end of the container, which has a concave or inwardly curved contour. The base member 34 is preferably bonded to the bottom end 14 of the container with adhesive, double sided tape, or similar bonding agent. In other embodiments, the dose counter may include a skirt that fits around the bottom of the container. Alternatively, as shown in FIG. 31, the base member, or other housing component, and the container may have substantially the same outer diameter, with an adhesive strip overlapping, and circumferentially surrounding, the base and container. The strip may be configured as a label, with various instructive and prescriptive information printed or applied thereto for viewing by the user. Various devices for securing the housing to the container are disclosed for example and without limitation in U.S. Pat. No. 7,341,057, the entire disclosure of which is hereby incorporated herein by reference. (No license, expressed or implied, is intended to be granted to either of this patent by reason of the incorporation by reference herein). In yet other embodiments, the dose counter is disposed in the bottom of housing 2, for example and without limitation in the space adjacent the support block 10. Such embodiments are disclosed for example and without limitation in U.S. Pat. No. 7,143,908, the entire disclosure of which is hereby incorporated herein by reference. (No license, expressed or implied, is intended to be granted to either of this patent by reason of the incorporation by reference herein).

Although the disclosed container and indicating device, and in particular, the cap member and base member, are shown as preferably having 'a circular cross section, those skilled in the art should understand that the container and indicating device, including any adapter, can be configured in other shapes, including for example, but not limited to, a rectangular, triangular, oblong cross-sections, etc.

As best shown in FIGS. 1, 2, 22, 23 and 36, the cap member 32 has a top portion with a viewing window 36 formed therein. Preferably, the cap member 32 is circular and the viewing window 36 is formed in the top portion adjacent the outer periphery of the cap member so as to overlie indicia applied to the top of one or more indicator members 40, 50 supported beneath the cap member. The viewing window can be configured in a number of various shapes. For example, the viewing window can be tapered, arcuate shaped, etc. In one embodiment, the viewing window is left open. In other embodiments, the viewing window is configured with a transparent window pane 42 that prevents tampering with the indicator members 40, 50 positioned beneath the window. In one embodiment, an upper surface of the window pane 42 lies flush with the outer surface of the cap member. In one embodiment, shown in FIGS. 22 and 41-43, the window pane 342 is formed by molding, for example a two-shot molding, with a molding tunnel gate 44 formed through a side of the cap member. The surface of the cap underlying the pane 342 may be configured with tapered (linear or curved) surfaces 46, and a pair of bottom shelves 48, which provides support for mating surfaces 346, 348 on the window pane 42, but also provide a greater viewing angle for the underlying dose counters. The pane may be made, for example and without limitation, of polycarbonate. In an alternative embodiment, shown in FIGS. 38-40, the window pane 442 may be configured with a pair of opposite tabs, or snap features, which engage a lip or rim on the cap member in a snap fit engagement. The pane 442 may also be configured with mating surfaces 346. In yet another embodiment, shown in FIG. 37, the pane 542 is provided with a pair of resilient arm members 544, each configured with a catch member 546 that engages the cap member with a snap fit. The pane is configured with a clear viewing portion 548 that frames the dosage indicia, and a frosted portion 550 surrounding the viewing portion. Preferably, the top surface of the pane is flush with the top surface of the cap member.

Referring to FIGS. 52 and 53, an alternative embodiment of a window pane 642 is shown as being installed from the side of the cap member 632, which has a flat portion 654 formed as a step opening to one side of the cap member. The pane 642 has a pair of locking features 644, or tabs, that engage corresponding recesses in the cap member by way of a snap fit. In addition, the pane includes a pair of opposite side ledges 646 that slide under and are engaged by corresponding overhangs 658 formed on the cap member. The pane 642 is installed by sliding it laterally relative to the cap member 632 such that the ledges 642 underlie the overhangs 658 and the tabs 644 are engaged with the recesses 648. The pane 642 has a clear portion 650 overlying the dosage indicia, and grained portions 652 to obscure read through outside the predetermined viewing area. The pane may be made of polycarbonate. As shown in FIGS. 58 and 60, another alternative of the pane has an upper ledge 690 or overlap portion that overlies the overhang 658 on the cap member. In addition, one of the locking features 644 may be omitted.

The top of the cap member may be configured with a plurality of grooved or raised portions 660 forming a grippable pattern for the user's thumb, or finger. In this way, the user can firmly press down on the cap member without slippage. One of skill in the art should recognize that other patterns or grippable surfaces, such as a knurled pattern, can be applied to the cap member to facilitate the use of the indicating device.

Referring to FIGS. 1, 2 and 8-11 the cap member 32 comprises a circumferential skirt 52 depending downwardly from the top portion. The skirt preferably has a smaller diameter than an upwardly depending skirt 54 of the base member, such that the cap member skirt 52 nests within the upwardly extending skirt 54 of the base member. Alternatively, the cap member can be configured with a skirt having a larger diameter than the skirt of the base member such that the base member skirt nests in the cap member skirt. The cap member is moveably mounted to the base member by way of a snap fit.

In particular, as shown in FIGS. 5, 8, 19 and 36, the cap member includes a plurality of engagement members 56 extending from an outer circumferential surface of the skirt. The cap member is inserted axially within the recess or cavity of the base member such that the engagement members, which have a tapered surface, slide past the rim of the base member skirt 54 until the engagement members are disposed in a plurality of pockets 58 formed along the inner circumferential surface of the base member skirt to form a snap-lock fit. In this way, the cap member is moveable with respect to the base member along an axial, or longitudinal, path defined by axis 26. Alternatively, the rim of the base member can be curved slightly inward such that the engagement members engage the inwardly curved rim portion so as to prevent the cap member from being separated from the base member.

The axial movement of the cap member 32 relative to the base member 34 is bounded or constrained by the engagement of the engagement members with the top of the base member pockets (or the base member rim) at a fully extended position and by engagement of a bottom rim 60 of the cap member skirt with the upper surface of the bottom portion, or with stop pads 61 formed along the inner circumferential sides of the base as shown for example in FIGS. 23 and 50. One of skill in the art should understand that the engagement members can alternatively be formed on the base member skirt so as to engage pockets or openings, or a rim (or like protrusion), formed on the cap member skirt.

As shown in FIG. 19, a spring 62 is disposed between the cap member and the base member. The spring 62 is preferably disposed around a downwardly extending hub portion 64 of the cap member, which receives an upwardly extending hub portion 66 of the base member. The hub portions forms a guidance system for the cap and base members. Preferably, the hub portions are proximately centered in the cap and base members, or relative close thereto, for example less than or equal to about 1.5 mm offset from the centerlines in one embodiment, and less than or equal to about 0.8 mm offset from the centerlines in another embodiment, which provides for a more uniform actuation force. Alternatively, the spring may be disposed interiorly of the hub portions, or the spring may be of such a size that the coils are positioned adjacent the inner circumferential surface of the cap member skirt. In an alternative embodiment, the hub of the cap is received in the hub of the base. The spring 62 functions as a return mechanism and biases the cap 32 member upwardly in the base member 34 such that the engagement members 56 of the cap member engage the upper portion of the pockets 58 of the base member. Although a compression spring is shown in the Figures, it should be understood that a belleville washer, cantilever, torsion, leaf and/or tension springs would also work to bias the cap member upwardly into engagement with the base member. The springs may be made of metal or plastic.

As shown in FIG. 8, a key member 68, or alignment rib, extends radially inwardly into the cap member hub portion 64, and is received in a key hole 70, or slot, formed in the hub portion 66 of the base member. During assembly, the key member 68 of the cap member is received in the key hole 70 of the base member so as to prevent rotation therebetween.

Referring to the embodiment of FIGS. 13-23, a first dosage indicator member 40 is rotatably mounted in the cap member about the axis 26 substantially parallel to the axial movement of the cap member relative to the base member. The indicator member 40 is generally open in the middle and includes a top portion having an upper surface 72 that rotatably slides along a bottom surface of the top portion of the cap member. Alternatively, the indicator member can be mounted on the outside of the cap member with a viewing window formed in the indicator member for viewing indicia applied to the top of the cap member.

As shown in the embodiments of FIGS. 13-23, the indicator member includes a circumferential skirt 74 depending downwardly from the top portion. A plurality of protrusions 76, or engagement tab members, extends from an inner circumferential surface of the cap member skirt and engages a rim 178 formed on the bottom of the indicator member skirt. Alternatively, the indicator member can include an engagement member, or rim, that engages a groove or similar opening in the cap member. In this way, the indicator member 40 is secured to the cap member 32 so as to prevent axial movement therebetween but where the indicator member is permitted to rotate relative to the cap member about axis 26. The indicator member is installed by snap-fitting the indicator member within the cap member. One of skill in the art should understand that the indicator member could alternatively be rotatably-mounted on the cap member hub portion (having a portion of the key member cut away), or on a similar axle secured to the cap member.

As shown in the embodiments of FIGS. 15, 23 and 48-49, the indicator member 40 has a plurality of inwardly and downwardly facing teeth 78 formed around the inner circumference of the skirt. The teeth may be formed about only a portion of the circumference, such that a gap greater than the pitch of the teeth is formed between some of the teeth.

As shown in the embodiments of FIGS. 15-17 and 54-56, the indicator member has a pair of indexing members 80, 680, configured as bumps extending radially outwardly from the circumferential skirt. In the embodiment of FIGS. 15-17, a flexible, circumferential portion 82 of the skirt, covering an angle α of about 60-90 degrees, is thinner than the remainder of the skirt 74, and further includes a circumferential opening 84 separating the flexible portion 82 from a portion of the skirt 86 longitudinally spaced therefrom and being of the same thickness of the remainder of the skirt 74. In this way, the flexible portions 82 of the skirt acts as a spring, which may be biased radially inwardly as the indexing member 80 moves past a corresponding one of a plurality of indexing features 88 (configured as indentations) formed around an inner circumferential surface of the cap member as the indicator member is rotated relative to the cap member. At the same time, the indexing action, and in particular the flexing of the skirt portion 82 is localized by the openings relative to the remaining skirt 74, 86, such that the indicator member 40 may still rotate smoothly and easily relative to the cap member 32. The angular distance between the indentations 88 is substantially the same as the angular distance between the plurality of indicator member teeth 78. In this way; the pair of indexing members 80 selectively engages the next indentation(s) 88 upon each incremental advancement of the indicator member defined by the distance between adjacent teeth 78. In one embodiment, the indentations 88 are formed as ratchet teeth which only permit one-way rotation of the indicator member relative to the cap member. It should be understood that one or more indexing members (two are disclosed) can be engaged with a plurality of indentations to control the rotational movement of the indicator member, regardless of whether the index members or indentations are formed on the cap member or the indicator member.

In the embodiment of FIGS. 54-56, a circumferential portion of the skirt 682 has a pair of longitudinal slits 686 that define a flexible tab 684, with the indexing member 680 extending radially outwardly from the end of the tab adjacent the rim of the indicator member. The flexible tab 684 flexes radially inwardly during an actuation, with the indexing member then self-centering in the indexing feature 88, formed as scalloped indentations, such that the dosage indicia on the face 690 of the indicator member are properly aligned in the viewing window.

As shown in FIGS. 1, 2, 15 and 30, dosage indicia 90, 152 in the form of numbers and color coding are provided on the top surface of the indicator member 40 and are visible to the user through the viewing window 36 and pane 42 provided in the top of the cap member. One of the skill in the art should understand that other indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, the indicator member 40 may be configured as a "tens" dose counter, with "tens" indicia formed around the indicator member from 200 to 10 (corresponding to the digits 20 to 1), with a final red indicia following the last ten (number 1) indicia so as to indicate that the container is empty. It should be understood that the indicia 90 can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container is empty, or, conversely, to go from the starting predetermined number to 0 (or some ending number), which again indicates to the user that the container is empty.

In one embodiment, the indicator member 40 is made of acrylonitrile butadiene styrene ("ABS"), which is receptive to certain alternative processes of printing or applying the indicia, including pad printing and hot stamping. The cap member and base member are preferably made of a hard plastic material such as Acetel, or clear polycarbonate.

Referring to FIGS. 12, 13, 20-29, 32-33 and 48-51, a drive mechanism 100 is shown as including a drive assembly. The drive assembly includes a second indicator member 50, 650, 750, 850 having a drive gear 102, 602, 702, 802 otherwise referred to as a ratchet wheel, integrally formed on a face thereof. In one embodiment, the ratchet wheel 102 includes axially facing ratchet teeth 104 formed in the face of the drive gear and disposed radially outwardly and around an axis of rotation 72. In an alternative embodiment shown in FIG. 21, the drive assembly includes a separate cogged drive gear 206 mounted coaxially with the second indicator member 50.

Figure 34:
FIG. 34 is a side view of an alternative embodiment of an indicator member.
Figure 33:
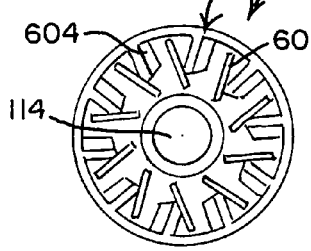
FIG. 33 is a side view of the indicator member shown in FIG. 32.
Figure 35:
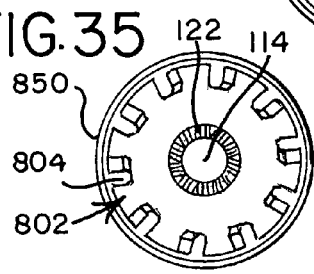
FIG. 35 is a side view of an alternative embodiment of an indicator member.

In the embodiment of FIGS. 32-33, 48, 49 and 51, and also the embodiment of FIG. 35, the teeth 604, 804 are formed around the periphery. In the embodiment of FIGS. 32, 33, 48, 49 and 51, a plurality of nesting pockets 604, or grooves are formed on the interior side face of the indicator at the same angular interval as, and adjacent to, the ratchet teeth 604. In the embodiment of FIG. 34, the ratchet teeth 704 are formed as spokes, or ridges, that extend axially inwardly toward a central hub.

In either embodiment, the indicator member is coaxially mounted to a drive member on an axle 108. The indicator member, drive member and axle can be made separately, with the drive gear/ratchet wheel and drive member then mounted on the axle, or all three parts can be integrally molded as a one-piece component. The drive assembly is preferably made of hard plastic material such as Acetel or polycarbonate. The indicator member is configured as a wheel and includes dosage indicia 106 positioned around the peripheral surface thereof. In one embodiment, the indicator member 50 is configured as a "ones" counter, with the indicia comprised of consecutive numerals running from 0 to 9 applied around the peripheral surface thereof.

In the various embodiments, the plurality of ratchet teeth 104, 604, 704, 804 (e.g., ten) are angularly spaced around the axis 72 on the face of the second indicator member. The drive member includes a single tooth 110 extending radially from the axle. The drive assembly is mounted to the cap member by engaging opposite ends 112, 114 of the axle with downwardly extending hub portions 116, 118 such that the axle, ratchet wheel and drive member rotate about an axis 72 substantially perpendicular to the axial movement of the cap member relative to the base member and to the axis of rotation 26 of the indicator member 40. Alternatively, the drive assembly can be mounted to the base member in a similar manner.

In some embodiments, shown in FIGS. 8, 9, 11, 24, 48 and 49, the cap includes a resilient, flexible support member 116, acting as a clevis, that partly or completely surrounds the axle and forms a journal bearing. The support member includes at least one second indexing feature 120, which releasably engaging at least one of a plurality of first indexing features 122 formed radially inwardly from the ratchet wheel 102, 702, 802 on the face of the second indicator member. In one embodiment, the support member includes an indexing feature 120 configured as a protuberance, or detent, while the first indexing features 122 are configured as recesses. In operation, the support member 116 is moveable (e.g., bendable) toward and away from the drive gear along an axial direction A defined by the axis 72 as the drive gear (and second indicator member) is/are rotated relative to the support member 116. At the same time, the support member biases the indexing features 120, 122 into engagement, and biases the indicator 50 member against the indicator member 40. The second indexing feature is successively engaged with the first indexing features as the drive gear is rotated relative to the support member. The opposite end of the axle is also completely surrounded and supported by a clevis. The indexing features of the support member and drive gear avoid the need for an additional non-return member to hold/restrain the rotation of the indicator member 50 between actuations. In addition, the flexible, resilient support member biases the second indicator member against the first indicator member, such that the combined indicia are assured of remaining close.

As shown in FIGS. 32, 33, 48, 49 and 51, the cap member may be configured with a resilient non-return member 620, which is configured with an end portion shaped, e.g., with a rib, to engage one of the nesting pockets 606 during a return sequence of the cap member so as to prevent the indicator member 50 from rotating as a pawl member moves past the ratchet teeth 604.

As shown in FIGS. 6, 7, 26 and 27, the drive mechanism further includes a drive member 124 having a pawl portion 126, extending laterally and shaped to engage at least one of the plurality of teeth. The drive member also includes a biasing portion 128, configured with a ramped surface 130. The drive member 124 is moveable relative to the indicator member from a preassembled position, wherein the pawl portion is positioned outside of a perimeter defined by the indicator member, to an assembled position, wherein the pawl is positioned inside of the perimeter and in registration with one of the ratchet teeth 104. During assembly, the biasing portion 128 is engageable with the indicator member 50 and biases the drive member (e.g., by bending the drive member), and in particular moves the pawl portion, outwardly relative to the indicator member 50 along the axis 72 of the axle as the drive member 124 is moved from the preassembled position to the assembled position. In this way, the pawl portion 126 can be properly interfaced and positioned relative to the drive gear 102 without having to use expensive and complicated tooling. Rather, the simple insertion of the cap member 32 relative to the base member 34 causes a simultaneous biasing (movement) and registration of the pawl member 126. The drive member 124, shown as a flexible rod or finger, extends upwardly from the bottom portion of the base member 34. After assembly, the biasing portion is positioned radially inwardly of the ratchet teeth 604 and does not interfere with the rotation of the indicator member 650.

In operation, the user depresses the cap member 32 from a fully extended position toward the base member 34 such that the cap member bottoms out in the base member at the bottom of the stroke and such that the base member imparts an axial load on the container 4 until a metered dosage is dispensed therefrom. In one embodiment, the biasing force of the spring 62 is less than the biasing force of the spring, located in the metering valve 24 of the container, such that the cap member first bottoms out in the base member with the container then being moved downwardly in the housing until a metered dose is dispensed. Alternatively, the container and the cap member may move together, but with the spring 62 force being less than biasing force of the spring operating on the metering valve.

As the cap member 32 is depressed toward the base member 34, the pawl portion 126 of the drive member 124 selectively engages the engagement surface of one of the ratchet wheel teeth 104, 604, 704, 804 and rotates the ratchet wheel 102 and integrally formed indicator member 50. In one embodiment, the support member 116 simultaneously flexes (e.g., bends) radially inwardly toward the hub 64 as the indexing features 120, 122 are advanced one feature. Alternatively, and referring to FIGS. 48, 49 and 51, the non-return member 620 is biased outwardly until the end portion 622 thereof is engaged with a next available nesting pocket 606. The user then releases the cap member, with the spring 62, or similar return mechanism, biasing the cap member 32 away from the base member 34 until the engagement member engages the base portion at the top of the stroke. When the cap member is released by the user, the container 4 is biased upwardly within the housing along the longitudinal axis 26 such that the valve stem 24 is moved to the closed position within the container. Simultaneously, as the cap member 32 is released and allowed to move away from the base member 34, the pawl portion 126 of the drive member is biased outwardly by the tapered surface of one of the teeth 104 on the ratchet wheel as the indexing features 120, 122, or engagement of the non-return member 620 with the nesting pocket 606, prevent a backwards rotation of the ratchet wheel and indicator member so as to maintain a unidirectional rotation of the ratchet wheel 102, 602, 702, 802 and integrally formed indicator member 50, 650, 750, 850. At the top of the stroke, the pawl portion 126 of the drive member is again placed in position for selective engagement with one of the teeth 104, 604, 704, 804 of the ratchet wheel. In this way, the ratchet wheel 102. 602, 702, 802, and connected drive member 110, are advanced an incremental amount for every actuation of the container 4 and the attendant release of medicament. The incremental amount is defined by and dependent on the number of teeth 104, 604, 704, 804 formed on the ratchet wheel. When formed with ten teeth, as shown in the preferred embodiment, the ratchet 102, 602, 702, 802 wheel will make one full revolution for every ten actuations of the indicator device and container 4, or a tenth of a revolution for each actuation. One skilled in the art will appreciate that the ratchet wheel can be provided with various numbers of teeth formed about its periphery such that the more or less axial movements or actuations of the container are required to make one full rotation of the ratchet wheel.

Alternatively, the operation of the ratchet wheel can be reversed. In this embodiment, the pawl 126 is biased outwardly by the tapered surface of one of the ratchet wheel teeth 104 on the downstroke, while a non-return member or indexing features prevent rotation of the indicator member. At the bottom of the stroke, the pawl is biased into engagement with one of the teeth. When the cap member is released by the patient, the spring, or equivalent return mechanism, biases the cap member upwardly within the base member along the longitudinal axis such that the pawl member engages one of the teeth and thereby rotates the ratchet wheel an incremental amount. In this embodiment, the indexing features maintain the rotational position of the ratchet wheel on the downstroke.

As shown in FIGS. 13, 19 and 28-29, the drive member 110 is shown as preferably having a single tooth or segment. Therefore, upon every tenth actuation, the drive member is rotated such that the tooth 110 selectively engages one of the teeth 78 formed on the indicator member so as to rotate the indicator member 40 an incremental amount. The incremental amount of rotation is defined by the distance between adjacent teeth 78, otherwise defined as the circular pitch of the teeth. In this way, the drive member 110 is selectively engaged with at least one of the teeth 78 of the indicator member after and upon a predetermined number of axial movements of the cap member 32 relative to the base member 34 so as to rotate the indicator member 40 the incremental amount. The predetermined number of axial movements required to cause the indicator member to rotate is defined by and dependent upon the reduction ratio of the ratchet wheel 102 and drive member 110, which, in turn, is defined by dividing the number of teeth formed on the ratchet wheel by the number of teeth formed on the drive member. For example, as shown in one embodiment, a ratchet wheel having ten teeth and a drive member having one tooth will result in an incremental movement of the indicator member 40, otherwise defined as the advancement of one tooth of the indicator member, upon every ten axial movements. Similarly, if the drive member had four teeth, and the ratchet wheel twenty, the predetermined number would equate to five axial movements, and so on. A one-to-one gear ratio would result in a predetermined number of one axial movement, wherein the indicator member would be moved upon every axial movement.

For example, in one embodiment of a container having 210 doses, wherein the ratchet wheel comprises ten teeth, ten actuations are required before the tooth engages a first tooth on the indicator member. During this sequence, as shown in one example of FIGS. 22 and 28, the "ones" counter is at four, while the "tens" counter is at 200. As the ones counter goes to "0," i.e., with the overall count going to "200," the "ones" indicator has completed a single cycle equal to the number of predetermined number of axial movements. On the next actuation, the "tens" indicator member 40 is moved incrementally, with the "ones" counter 50 moving to "9" and the "tens" counter to "19," so as to show a combined display of "199." The cycle is then repeated (by again making the predetermined number of axial movements) so as to again culminate in the incremental movement of the indicator member 40. At the end of the overall cycle, the indicator members 40, 50 count down to 1, and finally to a red (or any other color) zone indicia displayed on the "tens" counter 40 and a "0" displayed on the "ones" counter 50 as shown in FIG. 30.

The ratchet wheel 102 and drive member 110 with their reduction ratio provide a simple but reliable mechanism for advancing the indicator member 40. In particular, the indicator member can be made with fewer teeth than if it were required to advance upon every actuation of the indicator member and container. For ease of manufacturing, it is desirable to provide as coarse a pitch on each of the indicator member and ratchet wheel as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the container, it is important for the ratchet wheel and drive member to provide a relatively high reduction ratio, such that 200 linear reciprocal movements of the cap member and container correspond to one or less revolutions of the indicator member. As such, the indicator member 40 can be made with coarser teeth at less cost. In addition, larger coarser teeth interacting with a relatively large drive member tooth helps to improve the accuracy of the device as those parts mesh. In addition, the mechanism, and its attendant reduction ratio, permits the indicator member to make only a single revolution during the life of the container, i.e., until it is emptied, even when the container contains a relatively large number of metered doses (on the order of 200 or more doses).

Figure 28:
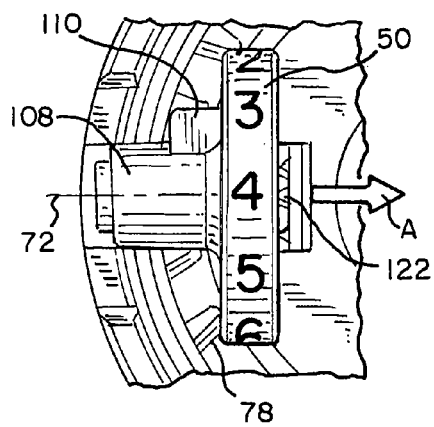
FIG. 28 is a partial, enlarged view of a support member interfacing with the second indicator member.
Figure 30:
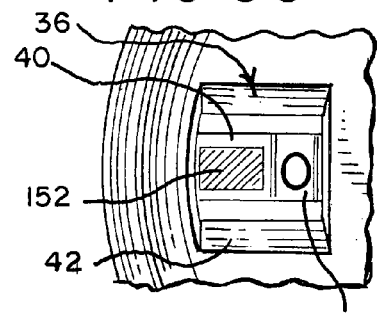
FIG. 30 is a partial, enlarged view of the display of dosage indicia through the viewing window as the end of use feature is engaged.

As shown in FIG. 30, the viewing window 36 is large enough such that the first and second dosage indicator members 40, 50 with their indicia are visible therein. In operation, the indicator member 50 rotates with each actuation of the cap member relative to the base member as the drive gear 102 is driven by the pawl portion 126 of the drive member 124. The indicator member 50 rotates about the axis 72 substantially perpendicular to the axial movement of the cap member relative to the base member and to the rotational axis 26 of the "tens" indicator member. In one embodiment, with the indicator member 1 having "ones" indicia and the ratchet wheel having ten teeth, the indicator member is advanced upon each actuation and provides indicia visible to the user to notify them of such advancement. As the indicator member completes a cycle, or rotation, the indicator member is advanced one increment by the drive member and the indicator member begins another cycle. In this way, the user is advised as to each actuation of the indicating device and the attendant dispensement of a dosage from the attached container.

While the indexing features 80, 88 prevent advancement of the indicator member 40 except upon engagement by the drive member 110 under normal operating conditions, the indicator member may be susceptible to unintended advancement between every predetermined number of actuations, e.g., every tenth actuation, since the indicator member 40 is not engaged by the drive member 110 except upon every tenth actuation. For example, if the device is dropped or falls, various forces may act on the cap member 32 to inadvertently rotate the tens counter 40 even though the requisite actuations have not occurred. For example and without limitation, if a dose counter with a reading of 198 is dropped, such that the tens counter is inadvertently advanced one increment, the visible indicia may then read 188 rather than 198, or 187 rather than 197 (assuming that one dose was actuated due to the fall), or even worse 168 rather than 198. To avoid this problem of a "count ahead," a movement limiter 140, configured as a finger extending upwardly from the base member 34, is disposed between adjacent teeth 78 of the indicator member 40 upon each actuation of the cap member relative to the base member. In this way, the movement limiter 140, acting as a fall arrestor, is operably engaged with the indicator member to prevent any rotation of the indicator member in response to the dose actuations occurring between the predetermined number of dose actuations. On the tenth actuation, the indicator member 40 is moved or rotated before the movement limiter 140 is moved between the next set of adjacent teeth. Alternatively, the movement limiter may be flexible enough that the indicator member bends the limiter to advance it one increment. In this way, the movement limiter 140 is reciprocally moveable along an axial direction 26 relative to the indicator member 40 in response to each of the actuations of the cap member 32 relative to the base member 34 occurring between the predetermined number of dose actuations. The physical presence of the movement limiter 140 between the teeth 78 of the indicator member 40 provides additional security against inadvertent rotation of the indicator member. Of course, the indexing features 80, 88 also prevent the indicator member 40 from inadvertently advancing, including for example when the movement limiter is not operably engaged with the indicator member, i.e., when not disposed between the teeth of the indicator member.

Referring to FIGS. 57-60, an alternative embodiment of a movement limiter, or drop arrestor, is shown. Therefore, as just explained, when the device is dropped on the cap member, all of the impact energy is transmitted to the counting mechanism. Depending on the relationship between the indicator members and drive member, the indicator member 640 may be inadvertently advanced by one or more decades not associated with a corresponding number of discharges of medication. This may result in a loss of count accuracy. To prevent this type of miscount, an arrestor brace 900 extends downwardly from the cap member. In one embodiment, the arrestor brace is configured as a post member, which has a greater resistance to bending than does the drive member 124.

During normal operation of the dose indicating device, the arrestor brace 900 does not interact with the indicator mechanism. As shown in FIGS. 59 and 60, the pawl portion 126 is engaged with one of the ratchet wheel teeth 604 and advances the indicator member 50. As the cap member 32 is moved toward the base 34, the arrestor brace 900 moves close to, but does not touch, the biasing portion 128, or the tip, of the drive member 124. As the cap member is released, the biasing portion 128, or tip of the drive member 124, clears the arrestor brace as the biasing portion 128 is biased away from the indicator member 50 as the pawl 126 slides over the tooth 604. Referring to FIGS. 57 and 58, under a high-energy drop condition, the pawl 126 drives the drive gear 50 with a very high impulse force, causing the indicator member 50 to have very high angular momentum, which may tend to force a tooth 604 into the pawl portion 126, thereby forcing the drive member 124 out of engagement and thereby allowing the indicator member 50 to skip ahead two or more increments. If the drive gear tooth 110 happens to be engaged with a tooth 78 on the indicator member 40, 640, the angular momentum of the indicator member 50 may likewise cause the indicator member 40, 60 to skip ahead two or more detents.

In operation, the arrestor brace 900 limits the backward flexing of the drive member 124 and pawl 126, with the pawl arresting or jamming up the indicator member 50, during a high-impact event when the cap member bottoms out in the base member. In this way, the mechanism may only count one increment, regardless of whether it is a normal actuation or a during a high-energy drop event. Upon release of the cap member 32, even after a high-energy drop event, the drive member 124 moves away from the cap member 32 with the biasing portion 128 clearing the arrestor brace 900 before the drive member 124 flexes back as the pawl 126 slides over a tooth 604.

Figure 29:
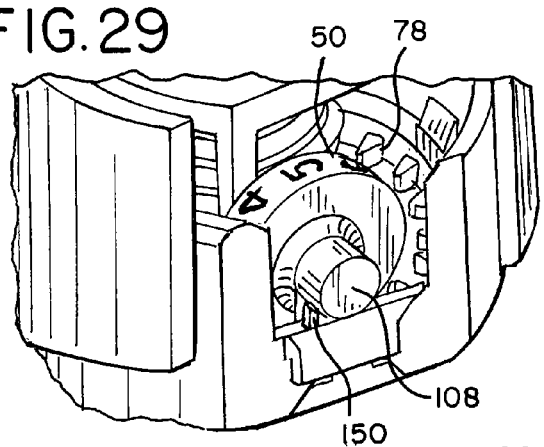
FIG. 29 is a partial, enlarged view of an end of use feature.

As shown in FIGS. 16, 18 and 29, the indicating device includes a lock device, or end of use feature. In particular, the indicator member includes a lock member 150, shown as a finger extending longitudinally from the circumferential skirt 74 in alignment with the end of use indicia, e.g., red zone indicia 152. In operation, the cap member 32 is moved towards and away from the base member 34 as described above so as to rotate the indicator member 40. During this operation, the lock member 150 is positioned inside the inner diametrical surface of the cap member 32 so as to not interfere therewith or otherwise restrain rotation of the indicator member 40. After the indicator member 40 has made one complete rotation, or has rotated to the point wherein the indicia indicate the container is empty, the lock member 150 is rotated into contact with the axle 72 of the drive assembly. In this position, the "tens" indicator member 40 cannot be rotated, which further prevents the "ones" indicator member 50, engaged therewith by way of drive member 110, from rotating. The pawl is then bent on the next actuation.

The medication delivery device described herein is suitable for dispensing of a drug formulation to a patient, as disclosed for example and without limitation U.S. Publication No. 2010/0313884, published Dec. 16, 2010, the entire disclosure of which is hereby incorporated herein by reference. The medication, or drug formulation, may take any suitable form and include other suitable ingredients such as diluents, solvents, carriers and propellants. Administration of a drug may be indicated for the treatment of mild, moderate or severe acute or chronic symptoms or for prophylactic treatment. It will be appreciated that the precise dose administered will depend on the age and condition of the patient, the particular drug used and the frequency of administration and will ultimately be at the discretion of the attendant physician. Embodiments are envisaged in which combinations of drugs are employed. Appropriate drugs may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propion yloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), salmefamol, carbuterol, mabuterol, etanterol, naminterol, clenbuterol, flerbuterol, bambuterol, indacaterol, formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α4 integrin inhibitors e.g. (2S)-3-[4-({[4-(aminocarbonyl)-1-piperidinyl] carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the drugs may be used in the form of salts, (e.g., as alkali metal or amine salts or as acid addition salts) or as esters (e.g., lower alkyl esters) or as solvates (e.g., hydrates) to optimise the activity and/or stability of the drug.

The drug formulation may in embodiments, be a monotherapy (i.e. single active drug containing) product or it may be a combination therapy (i.e. plural active drugs containing) product. Suitable drugs or drug components of a combination therapy product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other $β_2$-adrenoreceptor agonists, antiinfective agents (e.g. an antibiotic or an antiviral), and antihistamines. All suitable combinations are envisaged. Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propion yloxy-androsta-1,4-diene-17β-carbothioic acid S-(2-oxo-tetrahydro-furan-35-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-1,3-hydroxy-16α-methyl-3-oxo-17α-(2,2,3,3-tetramethycyclopropylcarbonyl)oxy-androsta-1,4-diene-17β-carbothioic acid S-cyanomethyl ester, 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester and 9α,21 dichloro-11β,17αmethyl-1,4 pregnadiene 3, 20 dione-17-[2'] furoate (mometasone furoate). Further corticosteroids are described in WO02/088167, WO02/100879, WO02/12265, WO02/12266, WO05/005451, WO05/005452, WO06/072599 and WO06/072600, all of which are hereby incorporated herein by reference.

Non-steroidal compounds having glucocorticoid agonism that may possess selectivity for transrepression over transactivation and that may be useful are disclosed WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398 and WO06/015870, all of which are hereby incorporated herein by reference. Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists), inhibitors of cytokine synthesis or 5-lipoxygenase inhibitors. Examples of iNOS inhibitors include those disclosed in WO93/13055, WO98/30537, WO02/50021, WO95/34534 and WO99/62875. Examples of CCR3 inhibitors include those disclosed in WO02/26722. Suitable bronchodilators are $β_2$-adrenoreceptor agonists, including salmeterol (which may be a racemate or a single enantiomer, such as the R-enantiomer), for instance salmeterol xinafoate, salbutamol (which may be a racemate or a single enantiomer, such as the R-enantiomer), for instance salbutamol sulphate or as the free base, formoterol (which may be a racemate or a single diastereomer, such as the R,R-diastereomer), for instance formoterol fumarate or terbutaline and salts thereof.

Other suitable $β_2$-adrenoreceptor agonists are 3-(4-{[6-({(2R)-2-hydroxy-2-[4-hydroxy-3-(hydroxymethyl)phen yl]ethyl}amino)hexyl]oxy}butyl)benzenesulfonamide, 3-(3-{[7-({(2R)-2-hydroxy-2-[4-hydroxy-3-hydroxymethyl)phenyl]ethyl}-amino)heptyl]oxy}propyl)benzenesulfonamide, 4-{(1R)-2-[(6-{2-[(2,6-dichlorobenzyl)oxy]ethoxy}hexyl)amino]-1-hydroxyethyl}-2-(hydroxymethyl)phenol, 4-{

(1R)-2-[(6-{4-[3-(cyclopentylsulfonyl)phenyl]butoxy}hexyl)amino]-1-hydroxyethyl}-2-(hydroxymethyl)phenol, N-[2-hydroxyl-5-[(1R)-1-hydroxy-2-[[2-4-[[(2R)-2-hydroxy-2-phenylethyl]amino]phenyl]ethyl]amino]ethyl]phenyl]formamide, and N-2 {2-[4-(3-phenyl-4-methoxyphenyl)aminophenyl]ethyl}-2-hydroxy-2-(8-hydroxy-2(1H)-quinolinon-5-yl)ethylamine, and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one. Preferably, the $\beta_2$-adrenoreceptor agonist is a long acting $\beta_2$-adrenoreceptor agonist (LABA), for example a compound which provides effective bronchodilation for about 12 hours or longer. Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160. Preferred phosphodiesterase 4 (PDE4) inhibitors are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl)cyclohexan-1-ol]. Other suitable drug compounds include: cis-4-cyano-4-[3-(cyclopentyloxy)-4-methoxyphenyl]cyclohexan e-1-carboxylic acid (also known as cilomalast) disclosed in U.S. Pat. No. 5,552, 438 and its salts, esters, pro-drugs or physical forms; AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Gong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585. Further compounds are disclosed in WO04/024728, WO04/056823 and WO04/103998, all of Glaxo Group Limited.

Suitable anticholinergic agents are those compounds that act as antagonists at the muscarinic receptor, in particular those compounds, which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds include the alkaloids of the belladonna plants as illustrated by the likes of atropine, scopolamine, homatropine, hyoscyamine; these compounds are normally administered as a salt, being tertiary amines. Other suitable anticholinergics are muscarinic antagonists, such as (3-endo)-3-(2,2-di-2-thienylethenyl)-8,8-dimethyl-8-azoniabicyclo [3.2.1]octane iodide, (3-endo)-3-(2-cyano-2,2-diphenylethyl)-8,8-dimethyl-8-azonia bicyclo[3.2.1]octane bromide, 4-[hydroxy(diphenyl)methyl]-1-{2-[(phenylmethyl)oxy]ethyl}-1-azonia bicyclo[2.2.2]octane bromide, (1R,5S)-3-(2-cyano-2,2-diphenylethyl)-8-methyl-8-{2-[(phenyl methyl)oxy]ethyl}-8-azoniabicyclo[3.2.1]octane bromide, (endo)-3-(2-methoxy-2,2-di-thiophen-2-yl-ethyl)-8,8-dimethyl-8-azonia-bicyclo[3.2.1]octane iodide, (endo)-3-(2-cyano-2,2-diphenyl-ethyl)-8,8-dimethyl-8-azonia-bicyclo[3.2.1]octane iodide, (endo)-3-(2-carbamoyl-2,2-diphenyl-ethyl)-8,8-dimethyl-8-azonia-bicyclo[3.2.1]octane iodide, (endo)-3-(2-cyano-2,2-di-thiophen-2-yl-ethyl)-8,8-dimethyl-8-azonia-bicyclo[3.2.1]octane iodide, and (endo)-3-{2,2-diphenyl-3-[(1-phenyl-methanoyl)-amino]-propyl}-8,8-dimethyl-8-azonia-bicyclo[3.2.1]octane bromide. Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118. Also of interest are revatropate (for example, as the hydrobromide, CAS 262586-79-8) and LAS-34273 which is disclosed in WO01/04118, darifenacin (CAS133099-04-4, or CAS133099-07-7 for the hydrobromide sold under the name Enablex), oxybutynin (CAS 5633-20-5, sold under the name Ditropan), terodiline (CAS15793-40-5), tolterodine (CAS 124937-51-5, or CAS124937-52-6 for the tartrate, sold under the name Detrol), otilonium (for example, as the bromide, CAS 26095-59-0, sold under the name Spasmomen), trospium chloride (CAS10405-02-4) and solifenacin (CAS 242478-37-1, or CAS 242478-38-2 for the succinate also known as YM-905 and sold under the name Vesicare).

Other anticholinergic agents include compounds disclosed in U.S. Ser. No. 60/487,981 and U.S. Ser. No. 60/511,009. Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine.

Exemplary H1 antagonists are as follows: Ethanolamines: carbinoxamine maleate, clemastine fumarate, diphenylhydramine hydrochloride, and dimenhydrinate. Ethylenediamines: pyrilamine amleate, tripelennamine HCl, and tripelennamine citrate. Alkylamines: chlropheniramine and its salts such as the maleate salt, and acrivastine. Piperazines: hydroxyzine HCl, hydroxyzine pamoate, cyclizine HCl, cyclizine lactate, meclizine HCl, and cetirizine HCl. Piperidines: Astemizole, levocabastine HCl, loratadine or its descarboethoxy analogue, and terfenadine and fexofenadine hydrochloride or another pharmaceutically acceptable salt. Azelastine hydrochloride is yet another $H_1$ receptor antagonist which may be used in combination with a PDE4 inhibitor.

The drug, or one of the drugs, may be an H3 antagonist (and/or inverse agonist). Examples of H3 antagonists include, for example, those compounds disclosed in WO2004/035556 and in WO2006/045416. Other histamine receptor antagonists which may be used include antagonists (and/or inverse agonists) of the H4 receptor, for example, the compounds disclosed in Jablonowski et al., *J. Med. Chem.* 46:3957-3960 (2003). Suitably, the drug formulation includes one or more of a $\beta_2$-adrenoreceptor agonist, a corticosteroid, a PDE-4 inhibitor and an anti-cholinergic. Generally, powdered drug particles suitable for delivery to the bronchial or alveolar region of the lung have an aerodynamic diameter of less than 10 micrometers, preferably from 1-6 micrometers. Other sized particles may be used if delivery to other portions of the respiratory tract is desired, such as the nasal cavity, mouth or throat. The amount of any particular drug or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The drugs for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1.5 mg per day. In one embodiment, the drug is formulated as any suitable aerosol formulation, optionally containing other pharmaceutically acceptable additive components. In embodiments, the aerosol formulation comprises a suspension of a drug in a propellant. In embodiments, the propellant is a fluorocarbon or hydrogen-containing chlorofluorocarbon propellant. Suitable propellants include, for example, $C_{1-4}$ hydrogen-containing chlorofluorocarbons such as $CH_2ClF$, $CClF_2CHClF$, $CF_3CHClF$, $CHF_2CClF_2$, $CHClFCHF_2CF_3CH_2Cl$ and $CClF_2CH_3$; $C_{1-4}$ hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$. Where mixtures of the fluorocarbons or hydrogen-containing chlorofluorocarbons are employed they may be mixtures of the above-identified compounds or mixtures, preferably binary mixtures, with other fluorocarbons or hydrogen-containing chloro-fluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$ hydrogen-containing fluorocarbons such as 1,1,1,2-tetrafluoroethane ($CF_3CH_2F$) and 1,1,1,2,3,3,3-heptafluoro-n-propane ($CF_3CHFCF_3$) or mixtures thereof. The drug formulations are preferably substantially free of chlorofluorocarbons such as $CCl_3F$, $CCl_2F_2$ and $CF_3CCl_3$. Preferably, the propellant is liquefied HFA134a or HFA-227 or mixtures thereof.

The propellant may additionally contain a volatile adjuvant such as a saturated hydrocarbon for example propane, n-butane, liquefied, pentane and is pentane or a dialkyl ether for example dimethyl ether. In general, up to 50% w/w of the propellant may comprise a volatile hydrocarbon, for example 1 to 30% w/w. However, formulations, which are free or substantially free of volatile adjuvants are preferred. In certain cases, it may be desirable to include appropriate amounts of water, which can be advantageous in modifying the dielectric properties of the propellant. A polar co-solvent such as $C_{2-6}$ aliphatic alcohols and polyols e.g. ethanol, isopropanol and propylene glycol, preferably ethanol, may be included in the drug formulation in the desired amount to improve the dispersion of the formulation, either as the only excipient or in addition to other excipients such as surfactants. In embodiments, the drug formulation may contain 0.01 to 5% w/w based on the propellant of a polar co-solvent e.g. ethanol, preferably 0.1 to 5% w/w e.g. about 0.1 to 1% w/w. In embodiments herein, the solvent is added in sufficient quantities to solubilise part or all of the drug component, such formulations being commonly referred to as 'solution' aerosol drug formulations. A surfactant may also be employed in the aerosol formulation. Examples of conventional surfactants are disclosed in EP-A-372,777. The amount of surfactant employed is desirable in the range 0.0001% to 50% weight to weight ratio relative to the drug, in particular, 0.05 to 10% weight to weight ratio. The aerosol drug formulation desirably contains 0.005-10% w/w, preferably 0.005 to 5% w/w, especially 0.01 to 2% w/w, of drug relative to the total weight of the formulation. In another embodiment, the drug is formulated as any suitable fluid formulation, particularly a solution (e.g. aqueous) formulation or a suspension formulation, optionally containing other pharmaceutically acceptable additive components. Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5. Suitable formulations (e.g. solution or suspension) may comprise one or more excipients. By the term "excipient", herein, is meant substantially inert materials that are nontoxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof. Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof; Suitable amino acids include non-polar amino acids, such as leucine and combinations and derivatives thereof. Suitable phospholipids include lecithins and combinations and derivatives thereof. Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof; Suitable solution formulations may comprise a solubilising agent such as a surfactant.

Suitable surfactants include α-[4-(1,1,3,3-tetramethylbutyl)phenyl]-ω-hydroxypoly(oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation. Suitable solution formulations may also comprise hydroxyl containing organic co-solvating agents include glycols such as polyethylene glycols (e.g. PEG 200) and propylene glycol; sugars such as dextrose; and ethanol. Dextrose and polyethylene glycol (e.g. PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation. Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij). Suitable solution formulations may also comprise one or more of the following components: viscosity enhancing agents; preservatives; and isotonicity adjusting agents. Suitable viscosity enhancing agents include carboxymethylcellulose, veegum, tragacanth, bentonite, hydroxypropylmethylcellulose, hydroxypropylcellulose, hydroxyethylcellulose, poloxamers (e.g. poloxamer 407), polyethylene glycols, alginates xanthym gums, carageenans and carbopols. Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin. Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate drug and optionally suspending agents, preservatives, wetting agents or isotonicity adjusting agents. Suitable suspending agents include carboxymethylcellulose, veegum, tragacanth, bentonite, methylcellulose and polyethylene glycols. Suitable wetting agents function to wet the particles of drug to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80). Suitable preservatives and isotonicity adjusting agents are as described above in relation to solution formulations.

The medicament dispensing device herein is in one embodiment suitable for dispensing aerosolized drug (e.g. for inhalation via the mouth) for the treatment of respiratory disorders such as disorders of the lungs and bronchial tracts including asthma and chronic obstructive pulmonary disorder (COPD). In another embodiment, the invention is suitable for dispensing aerosolized drug (e.g. for inhalation via the mouth) for the treatment of a condition requiring treatment by the systemic circulation of drug, for example migraine, diabetes, pain relief e.g. inhaled morphine. Administration of drug in aerosolized form may be indicated for the treatment of mild, moderate or severe acute or chronic symptoms or for prophylactic treatment. It will be appreciated that the precise dose administered will depend on the age and condition of the patient, the particular particulate drug used and the frequency of administration and will ultimately be at the discretion of the attendant physician. When combinations of drugs are employed the dose of each component of the combination will in general be that employed for each component when used alone. Typically, administration may be one or more times, for example from 1 to 8 times per day, giving for example 1, 2, 3 or 4 aerosol puffs each time. Each valve actuation, for example, may deliver 5 µg, 50 µg, 100 µg, 200 µg or 250 µg of a drug. Typically, each filled canister for use in a metered dose inhaler contains 60, 100, 120 or 200 metered doses or puffs of drug; the dosage of each drug is either known or readily ascertainable by those skilled in the art.

In another embodiment, the drug dispenser device herein is suitable for dispensing fluid drug formulations for the treatment of inflammatory and/or allergic conditions of the nasal passages such as rhinitis e.g. seasonal and perennial rhinitis as well as other local inflammatory conditions such as asthma, COPD and dermatitis. A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 µg, 50 µg, 100 µg, 200 µg or 250 µg of active drug. The precise dosage is either known or readily ascertainable by those skilled in the art.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A dose counter comprising:
   a housing;
   an indicator member rotatably mounted in said housing, said indicator member configured with dosage indicia;
   a drive gear associated with the indicator member and rotatable about an axis defining an axial direction, wherein said drive gear comprises a plurality of first indexing features disposed radially about said axis; and
   a support member rotatably supporting said drive gear, said support member comprising at least one second indexing feature releasably engaging at least one of said first indexing features, wherein at least a portion of said support member is moveable toward and away from said drive gear along said axial direction as said drive gear is rotated relative to said support member, and wherein said at least one second indexing feature is successively engaged with said first indexing features as said drive gear is rotated relative to said support member.

2. The dose counter of claim 1 wherein said support member comprises a resilient clevis, wherein said clevis is flexed toward and away from said drive gear as said at least one second indexing feature is successively engaged with said first indexing features.

3. The dose counter of claim 1 wherein one of said first or second indexing features comprises a recess, and wherein the other of said first or second indexing features comprises a protuberance shaped to engage said recess.

4. The dose counter of claim 1 wherein said drive gear is integrally formed with said indicator member.

5. The dose counter of claim 1 further comprising a pawl engaging at least one of a plurality of ratchet teeth formed on a face of said drive gear, wherein said plurality of ratchet teeth are disposed radially about said axis.

6. The dose counter of claim 5 wherein said ratchet teeth are positioned a greater radial distance from said axis than are said first indexing features.

7. The dose counter of claim 1 wherein said indicator member is a first indicator member, and wherein said support member biases said first indicator member against a second indicator member along said axis, wherein said second indicator member comprises dosage indicia.

8. The dose counter of claim 1 wherein said support member completely surrounds an axle supporting said indicator member and drive gear.

9. A medication delivery system comprising:
a container of medicament; and
a dose counter according to claim 1 coupled to said container.

10. A dose counter comprising:
a housing;
an indicator member rotatably mounted in said housing, said indicator member configured with dosage indicia, wherein said indicator member is rotatable upon a predetermined number of actuations, wherein said predetermined number is greater than one; and
a movement limiter operably engaged with said indicator member to prevent any rotation of said indicator member in response to said actuations occurring between said predetermined number of actuations.

11. The dose counter of claim 10 wherein said indicator member comprises a plurality of teeth, and wherein said movement limiter is moveable between a pair of said teeth upon each dose actuation.

12. The dose counter of claim 11 wherein said movement limiter is moveable toward and away from said indicator member along an axial direction defined by an axis of rotation of said indicator member.

13. The dose counter of claim 10 wherein said predetermined number is 10.

14. A medication delivery system comprising:
a container of medicament; and
a dose counter according to claim 10 coupled to said container.

15. A dose counter comprising:
a housing;
an indicator member rotatably mounted in said housing about an axis extending in an axial direction, said indicator member configured with dosage indicia, wherein said indicator member is rotatable about said axis upon a predetermined number of actuations, wherein said predetermined number is greater than one; and
a movement limiter reciprocally moveable along said axial direction relative to said indicator member in response to each of said actuations occurring between said predetermined number of actuations, wherein said movement limiter is operably engaged with said indicator member to prevent any rotation of said indicator member.

16. The dose counter of claim 15 wherein said indicator member comprises a plurality of teeth, and wherein said movement limiter is reciprocally moveable between a pair of said teeth upon each dose actuation.

17. A dose counter comprising:
an indicator member rotatable about an axis of rotation extending in an axial direction, wherein said indicator member comprises a face defining a circumferential perimeter and a plurality of teeth radially arranged on said face relative to said axis;
a drive member comprising a pawl portion shaped to engage at least one of said plurality of teeth, and a biasing portion, wherein said drive member is moveable relative to said indicator member from a preassembled position, wherein said pawl portion is positioned outside of said perimeter, to an assembled position, wherein said pawl is positioned inside of said perimeter, wherein said biasing portion is engageable with said indicator member, and biases said pawl outwardly relative to said indicator member along said axial direction, as said drive member is moved from said preassembled position to said assembled position.

18. The dose counter of claim 17 further comprising first and second housing components moveable relative to each other along a longitudinal direction positioned substantially perpendicular to said axial direction, wherein said indicator member is coupled to said first housing component, and said drive member is coupled to said second housing component, and wherein said drive member is moved along said longitudinal direction from said preassembled to said assembled position.

19. The dose counter of claim 18 wherein said first and second housing components are moveable along said longitudinal direction from a preassembled position to an assembled position.

20. The dose counter of claim 19 wherein said first and second housing components are reciprocally moveable relative to each other along said longitudinal direction when in said assembled position.

21. The dose counter of claim 17 wherein said biasing portion comprises a ramped surface.

22. A method of assembling a dose counter comprising:
moving a drive member relative to an indicator member along a first direction, wherein said indicator member is rotatable about an axis of rotation extending in an axial direction;
engaging a biasing portion of the drive member with said indicator member and biasing said drive member relative to the indicator member along said axial direction, said axial direction being substantially perpendicular to said first direction;
releasing said drive member; and
engaging said indicator member with a pawl portion of said drive member.

23. The method of claim 22 wherein said biasing portion comprises a ramped surface and wherein said engaging said biasing portion with said indicator member comprises sliding said ramped surface along a portion of said indicator member.

24. The method of claim 22 wherein said engaging said indicator member with a pawl portion comprises engaging at least one of a plurality of teeth arranged radially around said axis with said pawl.

25. A dose counter comprising:
a housing;
an indicator member rotatably mounted in said housing about an axis, said indicator member configured with dosage indicia around a circumferential surface thereof, said indicator member comprising a side face, wherein a plurality of ratchet teeth are formed in said side face, said ratchet teeth arranged circumferentially around and radially spaced from said axis, and wherein a plurality of nesting pockets are formed in said side face adjacent to and in alternating sequential spacing relative to said plurality of ratchet teeth, wherein said nesting pockets are arranged circumferentially around and radially spaced from said axis;
a pawl shaped and positioned to sequentially engage said ratchet teeth; and
a non-return member shaped and positioned to sequentially engage said nesting pockets.

26. The dose counter of claim 25 wherein said non-return member is engaged with at least one of said nesting pockets and prevents rotation of the indicator member as said indicator member is moved relative to said pawl member, and wherein said pawl is engaged with at least one of said ratchet teeth as said indicator member is moved relative to said non-return member.

27. A dose counter comprising:
a housing;
an indicator member rotatably mounted in said housing;
a drive gear operably coupled to said indicator member;
a pawl moveable toward and away from said drive gear during normal operation; and
an arrestor brace moveable adjacent said flexible pawl during a high-impact event, wherein said arrestor brace prevents said pawl from moving away from said drive gear during said high-impact event.

28. The dose counter of claim 27 wherein said indicator member and said drive gear are integrally formed.

29. The dose counter of claim 27 wherein said housing comprises a cap member reciprocally moveable relative to a base member, wherein said pawl is connected to said base member and said arrestor brace is connected to said cap member.

30. The dose counter of claim 29 wherein said drive gear is rotatably mounted to said cap member.

\* \* \* \* \*

UNITED STATES PATENT AND TRADEMARK OFFICE
CERTIFICATE OF CORRECTION

PATENT NO. : 9,202,164 B2
APPLICATION NO. : 13/626424
DATED : December 1, 2015
INVENTOR(S) : Marcus A. Sieffert et al.

It is certified that error appears in the above-identified patent and that said Letters Patent is hereby corrected as shown below:

On the Title Page

Left column, item (71), after "London" replace "(GB)" with --(CA)-- both occurrences.

Left column, item (72), after "London" replace "(GB)" with --(CA)-- both occurrences.

Signed and Sealed this
Fourteenth Day of June, 2016

Michelle K. Lee
*Director of the United States Patent and Trademark Office*